United States Patent
Hoffman et al.

(10) Patent No.: US 9,393,441 B2
(45) Date of Patent: Jul. 19, 2016

(54) RADIOPHARMACEUTICAL DELIVERY AND TUBE MANAGEMENT SYSTEM

(71) Applicant: MEDRAD, INC., Indianola, PA (US)

(72) Inventors: Raymond C. Hoffman, Gibsonia, PA (US); Barry L. Tucker, Verona, PA (US); David H. Berry, Kittanning, PA (US); Martin J. Uram, Pittsburgh, PA (US); Douglas DeScalzi, Pittsburgh, PA (US); Arthur E. Uber, III, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 452 days.

(21) Appl. No.: 13/831,734

(22) Filed: Mar. 15, 2013

(65) Prior Publication Data
US 2013/0331635 A1 Dec. 12, 2013

Related U.S. Application Data

(60) Provisional application No. 61/656,743, filed on Jun. 7, 2012.

(51) Int. Cl.
*A61M 5/00* (2006.01)
*A61N 5/10* (2006.01)
(52) U.S. Cl.
CPC ....... *A61N 5/1007* (2013.01); *A61N 2005/1021* (2013.01); *A61N 2005/1094* (2013.01)
(58) Field of Classification Search
CPC .......................... A61M 25/06; A61M 25/0612
USPC ........................................ 604/161, 177, 187
See application file for complete search history.

(56) References Cited

U.S. PATENT DOCUMENTS 2,725,058 A * 11/1955 Rathkey ............ A61M 25/0612
604/177
3,064,648 A * 11/1962 Bujan ............... A61M 25/0637
604/177

(Continued)

FOREIGN PATENT DOCUMENTS

| GB | 429365 A | 5/1935 |
|---|---|---|
| IT | RM96A000148 | 3/1996 |

(Continued)

OTHER PUBLICATIONS

The International Preliminary Report on Patentability of corresponding PCT Application No. PCT/US2013/044021.

(Continued)

*Primary Examiner* — John Lacyk
(74) *Attorney, Agent, or Firm* — Joseph L. Kent; David Schramm; James R. Stevenson

(57) ABSTRACT

A device for delivery of a radiopharmaceutical and delivery of a pharmaceutical agent are described. Various other components for delivery systems including tubing management systems, primer caps, diffusion chambers, radiation shields and syringe shields, needle handles, and other devices and methods are also described. Specifically, needle handles having a needle handle body attachable to a portion of a needle, and one or more wings or fins which are grasped by a user are described. The needle handle may be separated from the needle after insertion of the needle into a subject, and/or may provide access to a portion of tubing extending from the needle.

16 Claims, 39 Drawing Sheets

(56) References Cited

U.S. PATENT DOCUMENTS

| | | | |
|---|---|---|---|
| 3,584,625 A * | 6/1971 | Swick | A61M 25/065 604/161 |
| 3,885,560 A | 5/1975 | Baldwin | |
| 4,401,108 A | 8/1983 | Galkin et al. | |
| 4,409,966 A | 10/1983 | Lambrecht et al. | |
| 4,472,403 A | 9/1984 | Trijzelaar et al. | |
| 4,562,829 A | 1/1986 | Bergner | |
| 4,585,009 A | 4/1986 | Barker et al. | |
| 4,834,708 A * | 5/1989 | Pillari | A61M 25/0637 604/165.04 |
| 4,883,459 A | 11/1989 | Calderon | |
| 4,902,282 A | 2/1990 | Bellotti et al. | |
| 5,383,858 A | 1/1995 | Reilly et al. | |
| 5,472,403 A | 12/1995 | Cornacchia et al. | |
| 5,514,071 A | 5/1996 | Sielaff, Jr. et al. | |
| 5,520,653 A | 5/1996 | Reilly et al. | |
| 5,800,400 A * | 9/1998 | Hogan | A61M 25/0637 604/171 |
| 5,918,443 A | 7/1999 | Phillips | |
| 5,927,351 A | 7/1999 | Zhu et al. | |
| 5,947,890 A | 9/1999 | Spencer et al. | |
| 6,001,083 A * | 12/1999 | Wilner | A61M 25/0637 604/110 |
| 6,267,717 B1 | 7/2001 | Stoll et al. | |
| 6,450,936 B1 | 9/2002 | Smith, III et al. | |
| 6,471,674 B1 | 10/2002 | Emig et al. | |
| 6,520,930 B2 | 2/2003 | Critchlow et al. | |
| 6,522,144 B2 | 2/2003 | Boskamp | |
| 6,761,725 B1 * | 7/2004 | Grayzel | A61B 17/02 606/174 |
| 6,767,319 B2 | 7/2004 | Reilly et al. | |
| 7,018,363 B2 | 3/2006 | Cowan et al. | |
| 7,204,797 B2 | 4/2007 | Reilly et al. | |
| 7,611,486 B2 | 11/2009 | Jones et al. | |
| 7,731,106 B2 | 6/2010 | Doner et al. | |
| 7,905,861 B2 | 3/2011 | Rhinehart et al. | |
| 7,935,141 B2 | 5/2011 | Randall et al. | |
| 8,147,364 B2 | 4/2012 | Shioiri et al. | |
| 8,198,599 B2 | 6/2012 | Bouton et al. | |
| 2002/0012593 A1 | 1/2002 | Okuda | |
| 2003/0040700 A1 | 2/2003 | Hickle et al. | |
| 2007/0066937 A1 | 3/2007 | Jones et al. | |
| 2007/0088262 A1 | 4/2007 | Jones et al. | |
| 2007/0088272 A1 | 4/2007 | Jones et al. | |
| 2008/0177126 A1 | 7/2008 | Tate et al. | |
| 2010/0063481 A1 | 3/2010 | Hoffman et al. | |
| 2011/0021905 A1 | 1/2011 | Patrick et al. | |
| 2011/0132482 A1 | 6/2011 | Honma et al. | |
| 2011/0178359 A1 | 7/2011 | Hirschman et al. | |

FOREIGN PATENT DOCUMENTS

| | | |
|---|---|---|
| WO | 9842393 A1 | 10/1998 |
| WO | 0137904 A2 | 5/2001 |

OTHER PUBLICATIONS

The International Search Report and Written Opinion of corresponding PCT Application No. PCT/US2013/044021.
The International Preliminary Report on Patentability and Written Opinion and International Search Report mailed May 21, 2015 from corresponding PCT Application No. PCT/US2013/044038.
The International Preliminary Report on Patentability mailed Jun. 6, 2014 for corresponding PCT Application No. PCT/US2013/044021.
European Search Report dated Mar. 2, 2016 in EP13800649.

\* cited by examiner

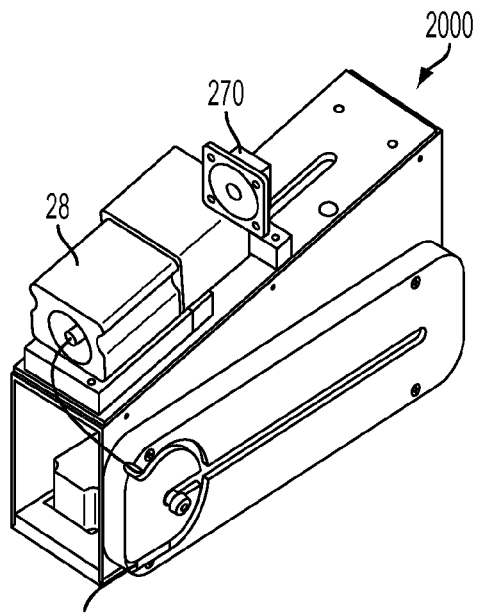
FIG. 2C-I
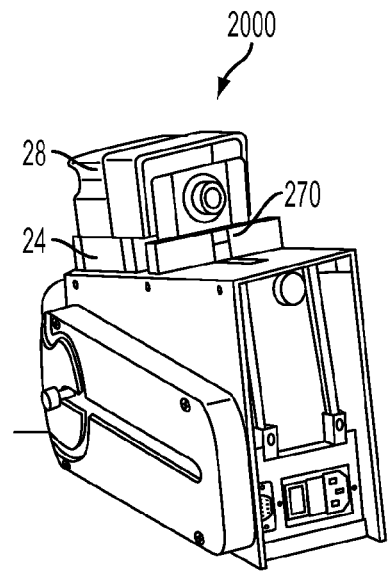
FIG. 2C-II
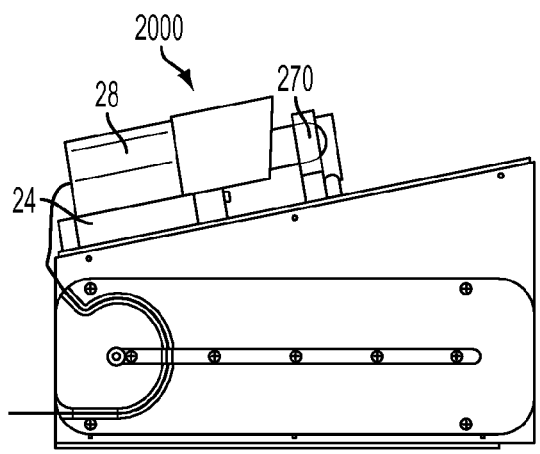
FIG. 2C-III
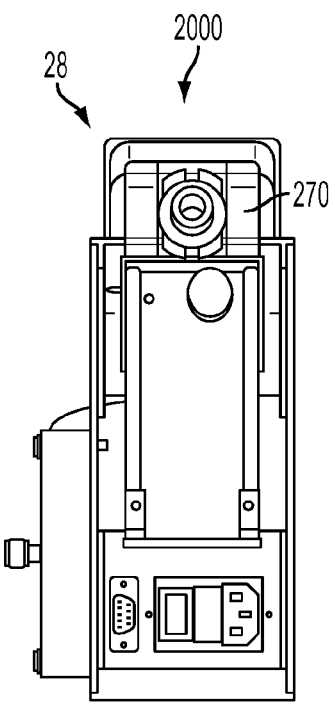
FIG. 2C-IV

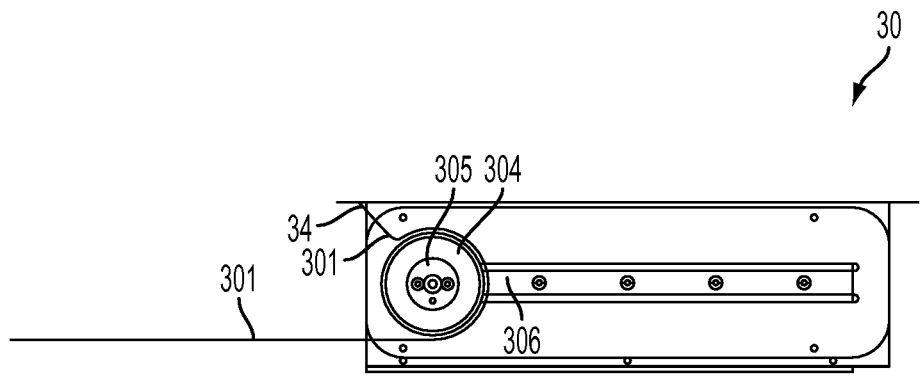
FIG. 3B-I
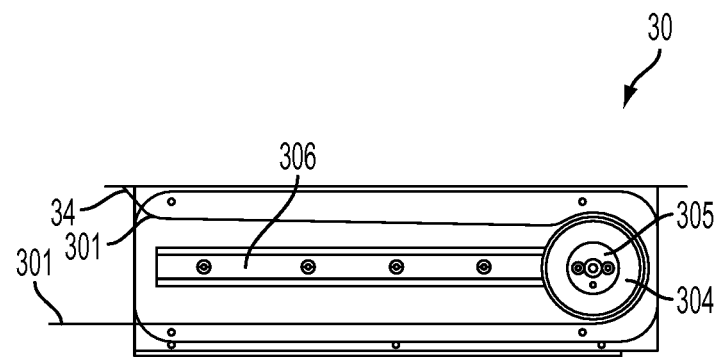
FIG. 3B-II

Syringe Information

Syringe Size: 3 mL

Drug Name: FDG

Fluid Type: ☐ RP

Lot Number: 567

Date: Today

Time: PM 2:00

Activity: 25.0 mCi

Cancel    Save

Subject Information

Subject ID

MICKEY

Alternate ID

M1

Gender

Male

Animal Type

Mouse

Cancel

Injection Complete

Prescribed
- μCi: 25.0
- μL: 6.4
- μL/s: 5.0

Delivered
- μCi: 26.3
- μL: 6.8

Injection Time: 4:11 PM
Protocol: FDG Low 25
Factor: --
Subject ID: MICKEY
Alternate ID: M1
Fluid Name: FDG
Lot #: 567

Repeat | Print | OK

FIG. 24

RADIOPHARMACEUTICAL DELIVERY AND TUBE MANAGEMENT SYSTEM

CROSS-REFERENCE TO RELATED APPLICATIONS

This application claims priority to U.S. Provisional No. 61/656,743 entitled "Radiopharmaceutical Delivery Device", filed Jun. 7, 2012, which is incorporated by reference herein in its entirety.

BACKGROUND

Radiopharmaceuticals are provided by manufacturers in numerous concentrations in sterilized containers (such as glass bottles or plastic packages) ranging incrementally in size from 20 ml to 200 ml. These containers are generally designed for a single use in which once a container is opened for a patient, then it is used for that patient only. The radiopharmaceutical is, generally, aspirated from such containers via a syringe pump used to inject the radiopharmaceutical, and any radiopharmaceutical remaining in the container is discarded to prevent infection with potentially contaminated radiopharmaceutical. The staff is faced with the task of choosing an appropriately sized container to assure an adequate injection while minimizing discarded radiopharmaceutical. Time consuming procedures are required to reload the syringe if more radiopharmaceutical is required than originally calculated, and expensive waste results if only a portion of a filled syringe is injected. In addition, staff are often exposed to hazardous radiation as a result of these procedures.

SUMMARY OF THE INVENTION

Various embodiments are directed to an injector including an injector body, a motor having at least one syringe actuating component configured to associate with a syringe attached to the injector body, a syringe mount attached to the injector body, and a syringe shield configured to reversibly attach to the syringe mount. In some embodiments, the syringe shield may include a first housing section having at least a forward portion including a syringe bore, a shoulder and a tubing access bore positioned at the forward end of the syringe bore, a plunger access bore at the aft end of the syringe bore, and an aft portion comprising a plunger access enlargement and a second housing section having at least a forward portion including a syringe bore, a shoulder and a tubing access bore positioned at the forward end of the syringe bore, a plunger access bore at the aft end of the syringe bore, and an aft portion comprising a plunger access enlargement. In such embodiments, reversible coupling of the first housing and the second housing may provide a forward syringe bore configured to encase a syringe and an aft plunger access enlargement configured to allow access to a plunger associated with the syringe.

In some embodiments, the injector body may be composed of steel, aluminum, or another metal or metal alloy, high tensile strength polymer compositions, and the like and combinations thereof. In some embodiments, the housing may be configured to cover the injector body. In certain embodiments, the syringe mount may include buttons, pins, slides, grooves, and the like configured to associate with the syringe shield and facilitate proper placement of the syringe shield within the injector body. In certain embodiments, the injector may include a control system operably connected to the motor and capable of causing the motor to expel contents from the syringe, and in particular embodiments, the injector may include a tubing management system.

Some embodiments are directed to a tubing management system including a tubing channel, a shield plate covering the tubing channel, at least one pulley positioned to move forward and aft within the tubing channel, a spindle extending through the pulley, a handle disposed on an end of the spindle extending through the shield plate, a slide contacting the spindle opposite the handle, and a track having an upper channel and a lower channel configured to accept the slide. In some embodiments, the pulley may include a circumferential groove, and in particular embodiments, the circumferential groove may include a large side wall and a short sidewall opposite the large side wall and wherein the short sidewall faces the shield plate. In certain embodiments, the shield plate may include a pulley channel extending to an edge of the shield plate. In some embodiments, the tubing management system may include a secondary tubing channel extending from an edge of the shield plate to the pulley channel. In particular embodiments, the tubing management system may include a retractor slot extending from the secondary tubing channel. In some embodiments, the tubing management system may include a pulley groove in cooperation with the pulley channel. In some embodiments, the tubing management system may include an upper shielded spacer and a lower shielded spacer operably connected to the shield plate. In various embodiments, the tubing management system may be configured and arranged to attach to an injector body.

Other embodiments are directed to a syringe shield including a first housing section having at least a forward portion including a syringe bore, a shoulder and a tubing access bore positioned at the forward end of the syringe bore, a plunger access bore at the aft end of the syringe bore, and an aft portion comprising a plunger access enlargement and a second housing section having at least a forward portion including a syringe bore, a shoulder and a tubing access bore positioned at the forward end of the syringe bore, a plunger access bore at the aft end of the syringe bore, and an aft portion comprising a plunger access enlargement. In some embodiments, reversible coupling of the first housing and the second housing may provide a forward syringe bore configured to encase a syringe and an aft plunger access enlargement configured to allow access to a plunger associated with the syringe. In various embodiments, the first housing section and the second housing section may be hingedly attached, and in certain embodiments, a radioactive emissions blocking material may be associated with at least the forward portion of the first housing section and forward portion of the second housing section. In some embodiments, a syringe may be completely or nearly completely encased by the radioactive emissions blocking material when the first housing section and the second housing section are coupled. In some embodiments, an aft groove may be configured to accommodate a flanged portion of a syringe associated with the plunger access bore. in certain embodiments, the syringe bore may be sized to accommodate a syringe having a diameter sufficient to hold 1 ml, 3 ml, 5 ml 10 ml, 15 ml, 20 ml, 30 ml, and combinations thereof. In some embodiments, the syringe shield may include a carrier handle capable of reversibly coupling to the syringe shield, and the carrier handle may include a carrier body having a grip portion, a tubing bore cover configured and arranged to fit within the tubing bore, and a plunger cover configured and arranged to associate with the plunger access enlargement. In some embodiments, the carrier handle may be integrally formed on the syringe shield. In particular embodiments, the first housing section and the second housing may include a groove or flange associated with the tubing bore and the carrier handle may include a tubing bore cover configured and arranged to fit within groove or flange. In certain embodiments, the tubing bore cover, the plunger cover, and combinations thereof may include a material capable of blocking radioactive emissions. In some embodiments, the tubing bore cover is hingedly attached to the carrier body, and in particular embodiments, a lever or button may be configured to allow the tubing bore cover to be released from the tubing bore or corresponding flanges and grooves on the syringe shield when the lever or button is depressed.

Further embodiments include a primer cap including a tube connector including a nut designed and configured to be grasped by a user, a first fitting operably connected to the nut, a bore extending from the first fitting though the nut, wherein the bore is designed to operably connect to a tube and to allow fluid flow from the tube through the nut, a cap including a handle designed to be grasped by the user and a sealing lip disposed on a surface of the cap opposite the handle, wherein the sealing lip is designed to create an airtight seal on the bore and facilitate a reversible connection between the cap and the bore. In some embodiments, a needle tubing section may be operably connected to the tube connector and fluidly connected to the bore. In particular embodiments, a needle may be operably connected to the needle tubing section opposite the tube connector, and in some embodiments, the tube connector may be physically attached to the needle tubing section by means such as, for example, soldering or gluing. In some embodiments, a second fitting may extend from the first fitting opposite the first fitting. In certain embodiments, the primer cap may further include a plug insert extending from a surface of the cap opposite the handle and designed and configured to be inserted into the bore.

Certain embodiments are directed to a primer cap including a tube connector including a nut designed and configured to be grasped by a user, a first fitting operably connected to the nut, a bore extending from the first fitting though the nut, wherein the bore is designed to operably connect to a tube and to allow fluid flow from the tube through the nut, and a cap including handle designed to be grasped by the user and a plug insert extending from a surface of the cap opposite the handle and designed an configured to be inserted into the bore. In some embodiments, a needle tubing section may be operably connected to the tube connector and fluidly connected to the bore. In particular embodiments, a needle may be operably connected to the needle tubing section opposite the tube connector, and in some embodiments, the tube connector may be physically attached to the needle tubing section by means such as, for example, soldering or gluing. In some embodiments, a second fitting may extend from the first fitting opposite the first fitting. In certain embodiments, the primer cap may further include a plug insert extending from a surface of the cap opposite the handle and designed and configured to be inserted into the bore.

Additional embodiments include methods for creating a wet-wet connection between tubing sections including the steps of introducing a needle tubing section into a blood vessel of a patient, wherein the needle tubing section includes a tube connector including a nut designed and configured to be grasped by a user, a first fitting operably connected to the nut, a bore extending from the first fitting though the nut, wherein the bore is designed to operably connect to a tube and to allow fluid flow from the tube through the nut, and a cap including a handle designed to be grasped by the user and a sealing lip disposed on a surface of the cap opposite the handle, wherein the sealing lip is designed to create an airtight seal on the bore and facilitate a reversible connection between the cap and the bore or a plug insert extending from a surface of the cap opposite the handle and designed an configured to be inserted into the bore, and removing the cap from the tubing connector. In various embodiments, an airtight seal may be created by the cap during the step of introducing. In some embodiments, a vacuum may be created in the bore drawing blood and other fluids from the subject into the needle tubing section. In particular embodiments, the methods may further include the step of connecting a tubing section to the tube connector.

Yet other embodiments are directed to a diffusion chamber including a tubing section, a first connector at a proximal end of the tubing section, a second connector at a distal end of the tubing section, wherein the second connector is configured to connect to a needle. In some embodiments, the tubing section may be clear or tinted. In certain embodiments, the needle may include a tubing section between the second connector and the needle. In particular embodiments, the tubing section is from about 1 inch to about 5 inches long.

Further embodiments are directed to a method for reducing contamination of a tubing section including introducing a needle tubing section into a blood vessel of a patient, wherein the needle tubing section includes a diffusion chamber designed and configured to allow a user to monitor diffusion of blood into the tubing section, a first connector at a proximal end of the tubing section, a second connector at a distal end of the tubing section, wherein the second connector is configured to connect to a needle, and removing the tubing section when blood from the patient reaches the first connector.

Still further embodiments are directed to a needle handle including a needle handle body configured to connect to a portion of a needle and one or more wings sized and shaped to be grasped by a user. In some embodiments, the needle handle may include a cleft including a breakable connection between portions of the needle handle body including each of the pair of separated wings. In particular embodiments, the one or more wings may include a pair of separated wings extending from a surface of the needle handle body, and in certain embodiments, a breakable cleft may be disposed opposite the separation. In some embodiments, the needle handle may include a needle tubing section, and the needle tubing section may include a connector opposite the needle handle.

DESCRIPTION OF DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

FIG. 2C are drawings of the internal frame of the injector body from various perspectives.

FIG. 3B is a drawing showing the pulley and slide portion of the tubing management system.

FIG. 11-FIG. 26 are screenshots exemplifying the user interface and workflow design associated with devices of the invention.

DETAILED DESCRIPTION

Figure 1:
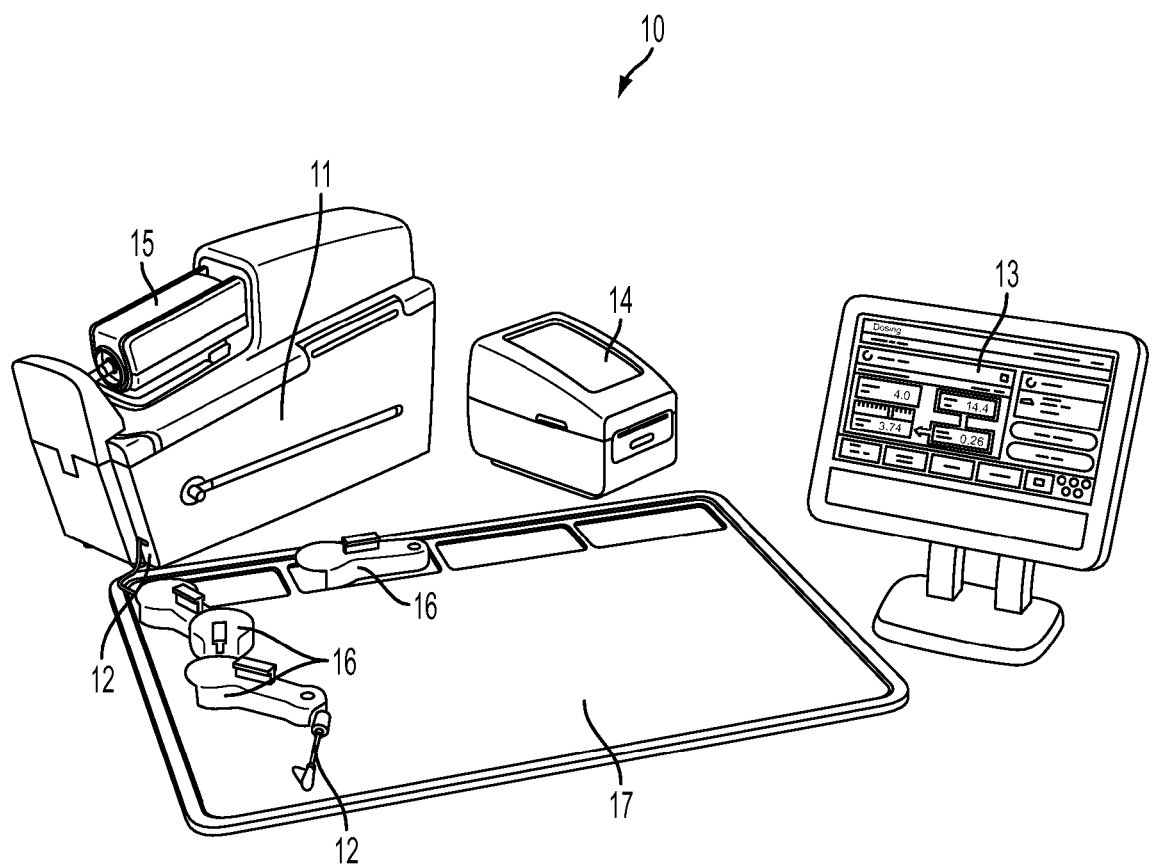
FIG. 1 is a drawing showing external features of the delivery system of some exemplary embodiments.

The above summary of the present invention is not intended to describe each illustrated embodiment or every possible implementation of the present invention. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

FIG. 1 shows an exemplary embodiment of a radiopharmaceutical delivery system 10 encompassed by the invention. In various embodiments, the radiopharmaceutical delivery system 10 may include a delivery injector body 11, one or more delivery tube sections 12, a display or graphical user interface ("GUI") 13, and a printer 14. In some embodiments, the radiopharmaceutical delivery system 10, may further include shielding components such as, but not limited to, syringe shielding 15, delivery tube shielding 16, and a shielded mat 17. In certain embodiments the radiopharmaceutical delivery system may further include a foot or hand switch (not shown) for operating the device. In some embodiments, the shielding components may be configured to reduce or eliminate exposure of the operator, subject, or other injected organism to radioactive emissions from the radiopharmaceutical. In other embodiments, shielding components may stabilize radiopharmaceuticals or optical tracers thermally and mechanically. For example, in some embodiments, shielding components may be designed to reduce or eliminate exposure of an optical tracer to light which can quench fluorescence and cause the tracer to become heated over time reducing the optical output of the tracer.

Figure 2A:
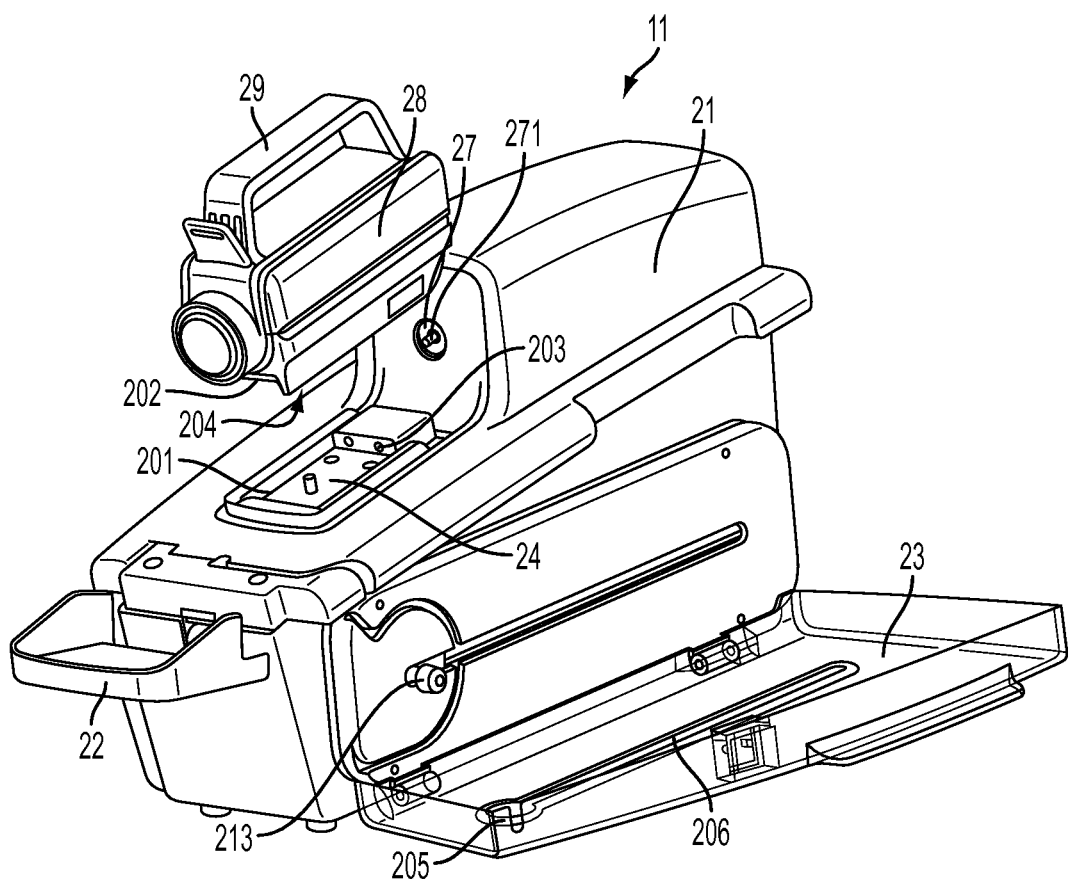
FIG. 2A is a drawing of an injector body showing the various features of the injector body, tubing management system, and syringe shield and syringe mount features of the injector body.
Figure 2B:
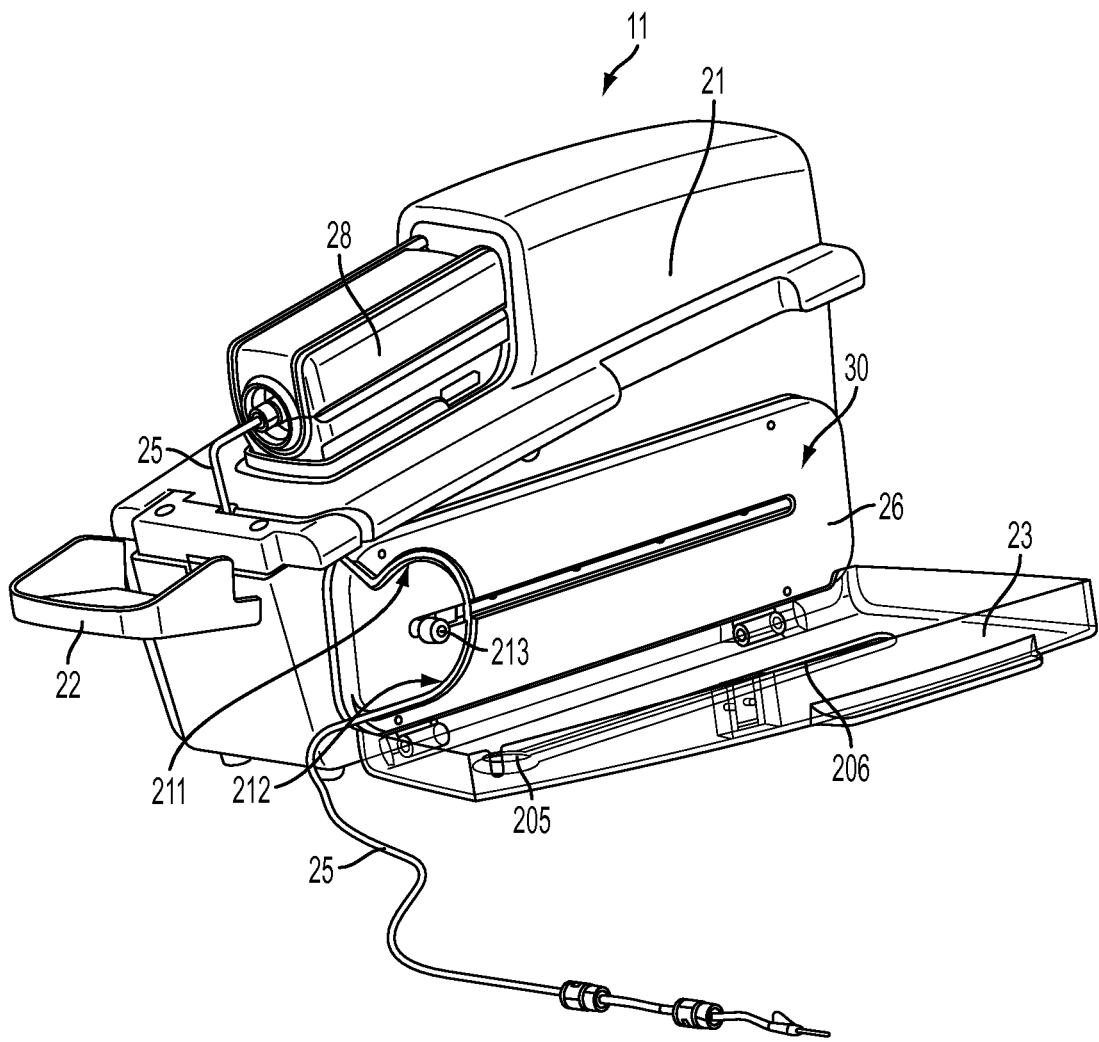
FIG. 2B is a drawing of an injector body showing a mounted syringe shield and tubing extension.

In some embodiments, the delivery injector body 11 may be configured as illustrated in FIGS. 2A and 2B. Generally, the delivery injector body 11 may include a housing 21, which may include one or more hinged access panels 22, 23 which allow the operator to access portions of the delivery injector body 11 covered by the housing or allow for improved access to exposed portions of the delivery injector body 11. In some embodiments, the hinged access panels may be shielded to reduce or eliminate emissions from radiopharmaceuticals positioned behind the access panel. For example, the syringe access panel 22 may include a thin layer of tungsten or another material capable of deflecting radioactive particles. In use, the syringe access panel may be angled to allow improved access to the syringe shield 28, as shown in FIGS. 2A and 2B. When the syringe has been placed within the syringe holder, the syringe access panel 22 may be rotated upwards to block emission from the syringe and delivery tubing 25. Similarly, a tubing access panel 23 may include shielding to block emissions from delivery tubing 25. In other embodiments, delivery tubing 25 within the delivery injector body 11 may be independently shielded by an integral tubing shield 26, and the tubing access panel 23 may not include a material to block radioactive emissions. In further embodiments, the housing may include hinged or slidable access panels for accessing motors or pumps for moving radiopharmaceutical through the delivery tubing and/or accessing ports for connecting, for example, a power cord, a controller, a computer, a memory device, a display, a hand switch or foot-switch, or various combinations thereof.

The delivery injector body 11 may further include one or more motors or pumps that are configured to associate with a syringe and effectuate delivery of the radiopharmaceutical. The motor or pump may be attached to the housing or a frame provided under the housing which maintains the position of the motor or pump during use or the radiopharmaceutical delivery system 10. The housing 21 may be removably attached to a frame and can be removed to allow access to components such as motors, pumps, syringe holders, tubing management systems without the need for an additional access panel. In some embodiments, a pump such as a peristaltic or in-line pump may be provided that attaches to tubing associated with a radiopharmaceutical storage container or syringe. Such a pump may be configured and positioned to effectuate discharge of the radiopharmaceutical through the tubing. In other embodiments, the delivery injector body 11 may include a motor having syringe actuation component 27, such as a piston. The actuation component may include a connector that can be configured to connect to the syringe or plunger portion of the syringe allowing the motor to advance or retract the plunger in the syringe. In certain embodiments as illustrated in FIG. 2A, the actuation component 27 may include a piston that contacts the plunger portion of the syringe and is capable of advancing the plunger but not retracting the plunger. In some embodiments, the actuation component may include one or more sensors 271 positioned to contact the plunger before or during actuation. Thus, in such embodiments, the motor may effectuate discharge of the radiopharmaceutical only.

The delivery injector body 11 may further include a syringe holder or mount 24. Embodiments are not limited to any particular syringe holder or mount. For example, in some embodiments, the syringe holder may be a device configured to accept and hold a syringe or vial holding the radiopharmaceutical by removably attaching to the syringe or vial body or flanges associated with the syringe or vial. In other embodiments, the syringe holder or mount may be configured to accept and hold a secondary device housing a syringe or vial including a radiopharmaceutical.

As illustrated in FIGS. 2A and 2B, a syringe shield 28 may include one or more flanges or grooves configured to associate with a syringe mount 24. FIG. 2A shows a syringe shield 28 operably connected to a shield holder 29 positioned to be inserted into a syringe mount 24. The syringe mount 24 of such embodiments may be in any configuration and may include, for example, buttons, pins, slides, grooves, and the like configured to associate with the syringe shield 28 to facilitate proper placement of the syringe shield within the delivery injector body 11. In certain embodiments, the syringe mount may include a forward groove or ridge 201 into which a corresponding ridge or groove 202 on the syringe shield 28 fits. The syringe mount 24 may further include rear binding 203 that associates with a groove or ridge 204 on the syringe shield 28. In some embodiments, the binding 203 may include a housing attached to the delivery injector body 11 that includes one or more springs positioned to urge a clamp forward against the groove or ridge 204 of the syringe shield 28 to lock the syringe shield 28 in place when it has been pushed into position.

In various embodiments, the syringe mount may be associated with and attached to a framework 2000 underlying the housing 21 rather than the housing itself. An example of such a framework 2000 is provided in FIG. 2C with individual illustrations I, II, III, and IV showing various perspectives of the framework 2000. The framework will generally be composed of a rigid material that provides mechanical support for the syringe mount 24 (shown with a syringe shield 28 mounted to the syringe mount 24) and the actuation component mount 270. Without wishing to be bound by theory, the framework may substantially improve the accuracy and reproducibility of injections by reducing or eliminating flexion that can occur when the syringe mount 24 and/or actuation component 27 are attached to a housing composed of a more flexible material. In some embodiments, the framework may be composed of steel, aluminum, or another metal or metal alloy or high tensile strength polymer compositions and may be designed to fit within the housing and provide attachment sites for mechanical components of the device in addition to the syringe mount and actuation component.

In still other embodiments, the housing 21 may include any number of grooves or opening that facilitate access to or movement of components of the delivery injector body 11. For example, in certain embodiments, the delivery injector body 11 may include a tubing management system, and the housing 21 may include an opening 205 and groove 206 that allows a portion of the tubing management system, such as the handle 213 illustrated in FIGS. 2A and 2B, to protrude from within the delivery injector body 11 to facilitate manual movement of portions to the tubing management system.

Figure 3A:
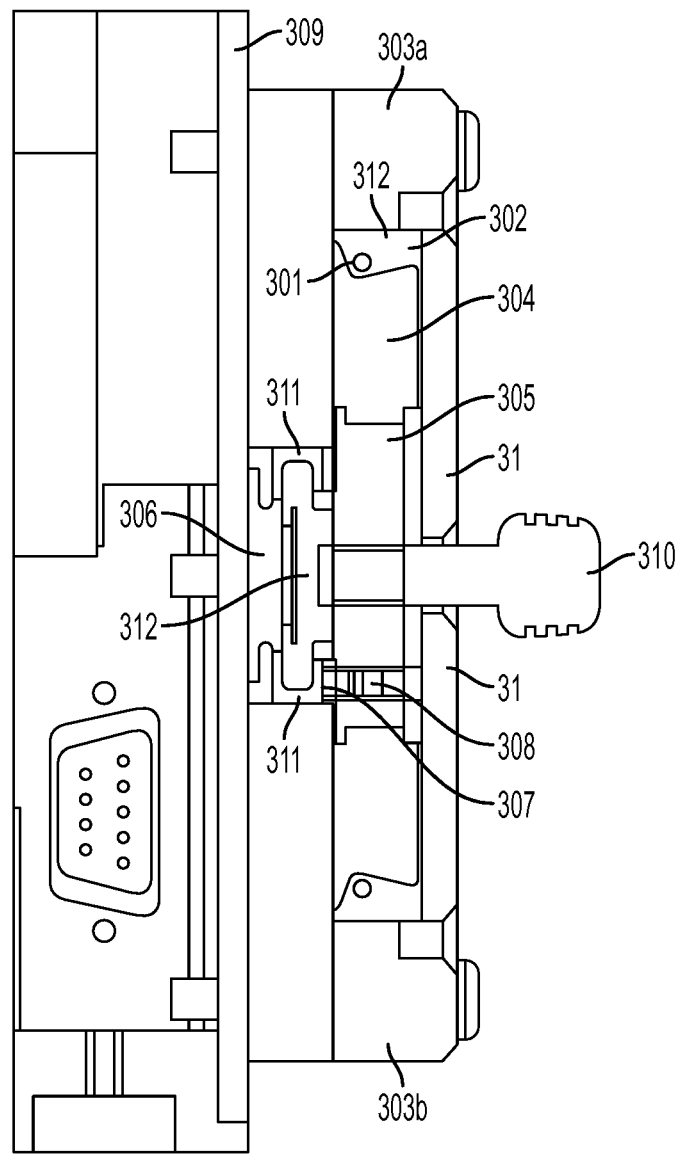
FIG. 3A is a drawing of the internal features of the tubing management system.

FIG. 3 shows another exemplary embodiment of a tubing management system 30. FIG. 3A shows tubing management system having a shield plate 31 configured and arranged to cover a tubing channel 302 through which the extension tube 301 can be passed. The shield plate may be spaced from the delivery injector body or frame underlying the injector body 309 using upper and lower shielded spacers 303a, 303b. The extension tube 301 may be passed through and maintained in the tubing channel 302 by any means, and in some embodiments the amount of extension tubing 301 released from the tubing management system may be controlled by a pulley system. As illustrated in FIG. 3A, the pulley system may include at least one pulley 304 positioned to move forward and aft within the tubing channel between the shield plate 31 and the injector body or framework 309.

In particular embodiments, the pulley 304 of the pulley system may be shaped to guide the extension tube while within the tubing channel 302. For example, as illustrated in FIG. 3A, the pulley 304 may be shaped to provide a groove that is offset with a larger side wall being positioned on the side of the pulley 304 closest to the body or framework 309. A shorter side wall may be provided opposite the larger side wall facing the shield plate 31. In this arrangement, tubing may be inserted into the tubing management system 30 through the short side wall where the tubing contacts the groove. During operation, the tubing will remain within the groove, and the larger side wall will prevent the tubing from becoming displaced from the groove and getting caught between the pulley 304 and the body or framework 309 where it can bind the system and prevent movement of the pulley 304 and spindle 305. At the same time, the shorter side wall allows access of the tube to the pulley 304 groove for loading and unloading the extension tube 301.

A spindle 305 may be provide within the pulley 304 and may include a handle 310 extending away from the delivery injector body or framework 309 and through the shield plate 31. The pulley 304 may be positioned on the spindle to allow the pulley 304 to rotate freely while the user moves the pulley within the channel 302 using the handle 310. Opposite the handle, the spindle 305 may contact a slide 306. The slide may be in any configuration that controls lateral and up and down movement of the spindle 305 while the pulley 304 is moved forward and aft. For example, in some embodiments, a track having upper and lower channels 311 may be configured to accept a spindle extension 312 and allow the spindle extension to slide within the upper and lower channels 311 allowing for forward and backward movement of the spindle 305 and pulley 304 while eliminating or reducing upward, downward, and lateral movement.

In some embodiments, the pulley and spindle system, pulley 304, spindle 305, spindle extension 312, and associated slide 306 and upper and lower channel 311, may further include a set screw 308 positioned within the spindle such that friction between the track and the spindle can be increased by increasing the tension on the set screw 308, i.e., turning the set screw into the track. The set screw may allow the user to control the movement of the pulley spindle system such that the pulley 304 moves easily within the tube channel 302, but sufficient friction is created between the moving parts such that the pulley does not move through the channel without force from the user. Therefore, bumping the delivery injector body 309 will not cause unintended discharge of the tube 301 in the channel. Friction can also be controlled by providing bearing material 307 between the spindle 305 and the pulley 304 and spindle extension 312. Such bearing materials 307 are well known in the art and can be selected to allow sufficient rotational friction to avoid unwanted release of the extension tube 301 while allowing easy movement of the pulley 304 within the tube channel 302.

Operation of the tube management system is illustrated in FIG. 3B. In position I., the spindle 305 and pulley 304 may be positioned at the forward end of the slide 306. The extension tube 301 may be inserted through a retractor slot 34 and entering through the top from the tube management system 30, around the pulley 304, and exiting at the bottom. The spindle 305 and pulley 304 may be slid from the front of the system to the back as illustrated in position II. The tubing 301 may be maintained within a groove associated with the pulley 304 while the pulley 304 rotates about the spindle 305 allowing the tubing extension to easily travel through the tubing management system 30.

Figure 3C:
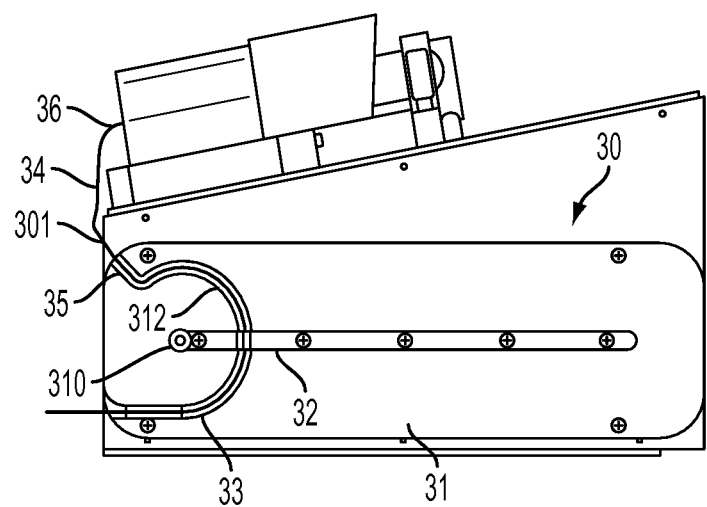
FIG. 3C is a drawing showing the tubing shield portion of the tubing management system.

The shield plate 31 may include a number of external features as illustrated in FIG. 3C. For example, in some embodiments, the shield plate 31 may include a side channel 32 extending from the front to the back of the shield plate 31. The side channel may be configured to allow the handle 310 attached to the spindle 305 and pulley 304 to pass through the channel 32 and slide from the front to the back of the shield plate 31, and vice versa, without hindrance. The shield plate 31 may further include a pulley channel 33 at the forward end of the shield plate 31. The pulley channel 33 may be positioned such that a groove associated with the pulley 304 and configured to accept the extension tube 301 can be accessed only when the pulley 304 is at the forward most position allowed by the side channel 32. In some embodiments, the pulley channel 33 may have a circular or semi-circular shape such that the pulley channel 33 and the groove are continuous with one another when the pulley 304 is at its forward position. The pulley channel 33 may further run to the outer edge of the shield plate and proved a channel for the extension tubing 301 to exit the tube channel 302.

In some embodiments, a secondary channel 35 may be provided to improve access of the tubing to the pulley channel 33. In such embodiments, the secondary tubing channel 35 may be provided at an angle from the pulley channel 33 and may extend from an outer edge of the shield plate 31 to the pulley channel 33. In further embodiments, a retractor slot (not shown) may be provided within the delivery injector body 11 that is configured to accept the extension tubing 301 and encase the extension tubing 301 from the syringe connector to the secondary tubing channel 35 providing shielding between the syringe connector 36 and the secondary tubing channel 35.

In operation, the user may connect an extension tube 301 to the syringe connector 36, insert the extension tube into the shielded retractor slot 34, and through the secondary tubing channel 35. The extension tubing 301 may then be introduced into the pulley groove 312 through the pulley channel 33 and out of the pulley groove 312 through a the extension of the pulley channel 33 extending to the edge of the shield plate 31. In some embodiments, a groove associated with the secondary channel 34 and the pulley channel 33 may be provided to ease insertion of the extension tube and direct the user's finger during insertion of the extension tube 301 into the pulley groove 312. After the extension tubing has been seated within the pulley groove 312, the user may move the pulley 304 backward through the tubing channel 302 causing the extension tubing to be carried with the pulley into the tubing channel 302 and behind the shield plate 31. The extension tubing is thereby retracted. To release the extension tubing from the tubing management system 30, the user may tug on the tubing extension pulling the pulley 304 forward and allowing the extension tubing to be discharged. To retract, the pulley 304 may be moved backward into the tubing channel 302 using the handle 310.

The extension tubing 301 may be prepared from any material known an used in the art, and in certain embodiments, the extension tubing may be, for example, medical grade polyvinyl chloride (PVC), polyurethane, polyethylene, polypropylene, or silicone. The extension tubing 301 may be clear or opaque depending on the material to be delivered. For example, in embodiments in which an optical tracer is administered using the delivery device, the tubing extension 301 may be tinted or colored to block light that can degrade the optical tracer. Thus, the tubing extensions may include one or more dyes, colorants and/or pigments, and in certain embodiments the tubing may be black.

As provided in FIG. 1, the radiopharmaceutical delivery system 10 of some embodiments may include a display 13. Such a display 13 may be a color display or a black and white display. In some embodiments, the display 13 may be configured to allow a user to program or otherwise operate the system 10, and in various embodiments, the display 13 may display real-time data with regard to the operation of the system. For example, in certain embodiments, the display 13 may have touch-screen capabilities or be otherwise configured to allow a user to interact with the system and, in particular, a computer used to control the system, by manipulating or touching the display 13. In other embodiments, the system may include a keyboard, mouse, or other device configured to allow the user to program or otherwise operate the system. In still other embodiments, the display may be included as part of a laptop, smartphone, or tablet computer that is electronically associated to the system by a hard wired or wireless network. The display 13 may be fixed to the delivery injector body 11, and in other embodiments, the display may be positioned away from the system and attached to the system by a hard wired or wireless network. Such displays 13 may be configured to be tilted or swiveled to allow the display 13 to be positioned by an operator.

In some embodiments, the display 13 can be configured to present or provide data and information to an operator in an intelligible form or format, i.e., visually display this information and data in electronic form. In certain embodiments, the radiopharmaceutical delivery system 10 may include a printer 14 which is configured to physically display this information and data in print form. The printer of various embodiments may be of any type and includes off the shelf ink-jet and laser printers. In particular embodiments, the printer may be configured to print adhesive backed labels. In still other embodiments, the radiopharmaceutical delivery system 10 may include a speaker (not shown) to audibly present this information and data in audible form. For example, a speaker may be configured to produce an audible "beep" when an injection is complete, or when the radiopharmaceutical has been used up or is nearly used up. In various embodiments, such devices may be in communication with the computer or other control system through output interfaces.

Figure 4A:
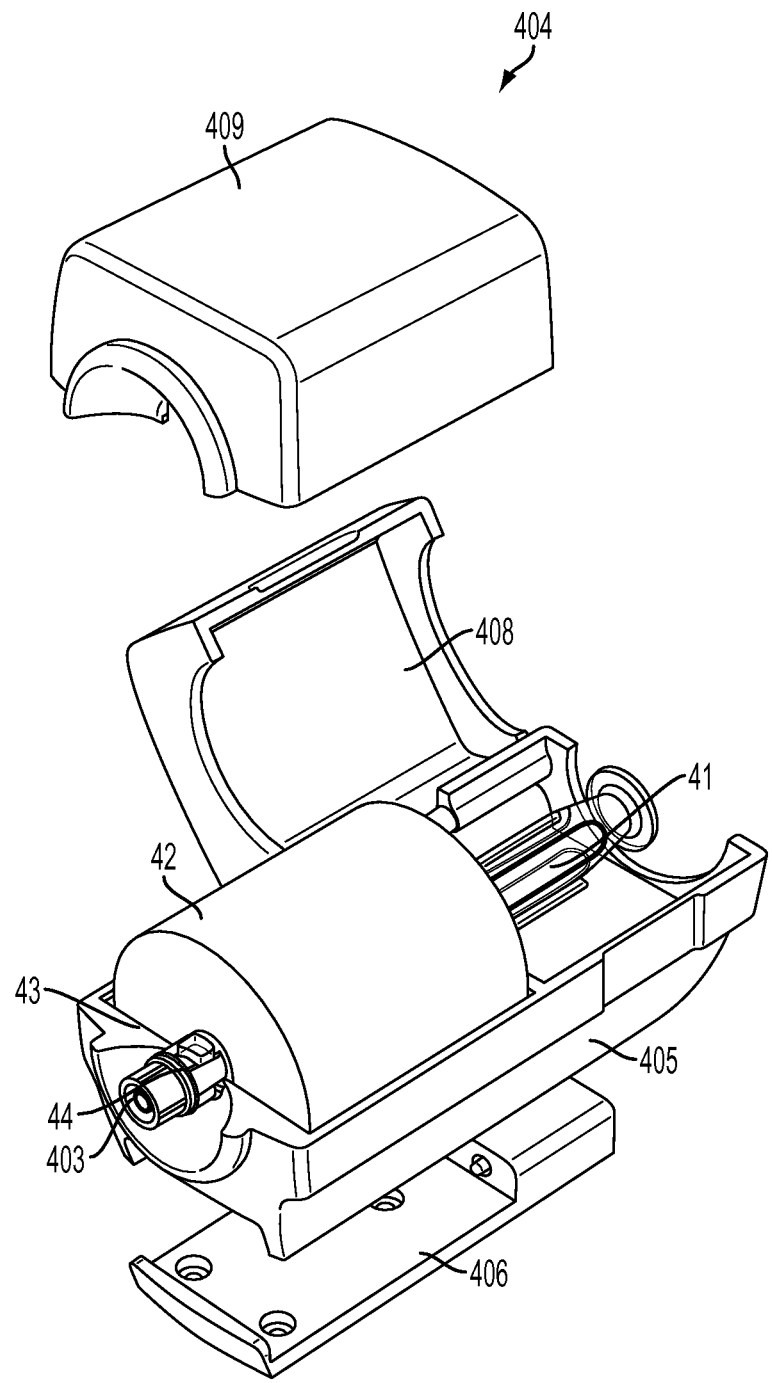
FIG. 4A is a drawing showing an embodiment of a syringe shield.

Various embodiments include a syringe shield 28 (FIG. 2). FIG. 4 shows various embodiments of such a syringe shield 28 in more detail. In some embodiments as illustrated in FIG. 4A, a syringe 41 may be inserted into a syringe shield 42 having a bored portion sized and shaped to accept the syringe 41. The syringe shield may further include a shoulder 43 configured to properly position the syringe within the forward portion of the syringe shield 42, and a tubing bore 44 configured to allow access to a portion of the syringe 41 designed to attach to tubing (not shown). The syringe shield 42 of such embodiments may attach to the delivery injector body 11 using the syringe mount system described above, or in other embodiments, they may attach to the delivery injector body 11 through a saddle mount which may be shaped to fit within a groove provided on the syringe shield 42. In some embodiments, the saddle mount may include pressure fittings, grooves, pins, buttons, and the like that facilitate reversible attachment of the syringe shield 42 to the saddle mount.

The shield provided in FIG. 4A further includes a syringe shield 404 into which the syringe shield 42 is placed. In some embodiments, the syringe shield 404 may include a lower portion 405 that is configured to reversibly attach to a syringe mount 406. The syringe shield 404 may also include an upper portion that can include one or more removable or hinged segments 408. In some embodiments, the upper portion may be attached to the lower portion by a single hinge that allows access to the syringe shield 42 and the syringe 41. In other embodiments, the upper portion may be attached to the lower portion by pressure fittings, and the upper portion may be removed from the lower portion to allow access to the syringe shield 42 and syringe 41. In still other embodiments, the upper housing of the syringe shield 404 may include a hinged syringe access door 408 that allows access to part of the internal segments of the syringe shield 404. For example, as illustrated in FIG. 4A a hinged access door 408 may allow access to the syringe 41 such that the user can more easily maneuver the syringe while inserting it into the syringe shield 42. The forward portion of the upper housing 409 may be positioned to cover the syringe shield 42 and may be fixedly attached to the lower housing 405. In this arrangement, only the hinged part of the upper housing 408 is movable.

Figure 4B:
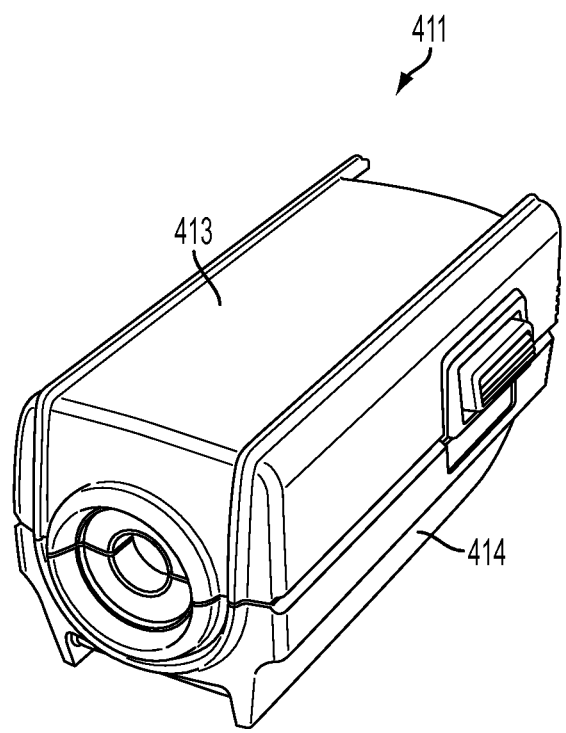
FIG. 4B is a drawing showing a second embodiment of a syringe shield having latched, clam shell syringe access.
Figure 4B:
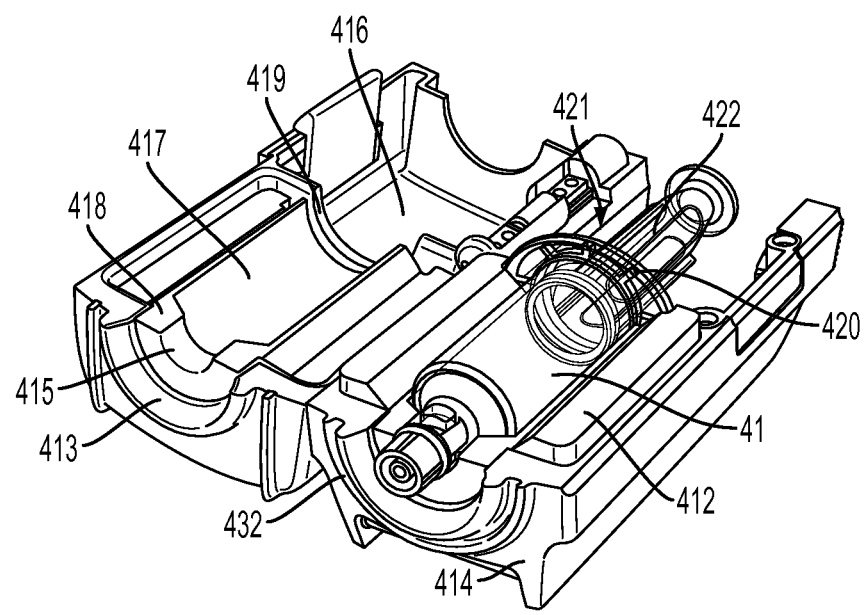

In still further embodiments, the syringe shield may be incorporated in the syringe shield housing. As illustrated in FIG. 4B, in some embodiments, the syringe shield 411 may be designed to include a radioactive emissions blocking material 412 in the upper housing 413 and lower housing 414. As illustrated, the upper housing 413 in such embodiments or any part thereof can be hingedly attached to the lower housing to allow access to the syringe. The radioactive emissions blocking material may be incorporated into the syringe housing such that the syringe is completely or nearly completely encased by the radioactive emissions blocking material when the housing is in the closed position. In such embodiments, a tubing access bore 415 and plunger access point 416 may be provided to allow access of the syringe to tubing and motor/pump portions of the radiopharmaceutical delivery system 10. In some embodiments, the syringe may be seated in a syringe bore 417 that is configured and designed to accommodate a syringe. Such a syringe bore may include a shoulder 418 positioned to contact a front portion of the syringe, the syringe bore 418 may further include an aft groove 419 configured to accommodate a flanged portion 420 of the syringe 41 associated with the plunger access bore 421. The plunger 422 may fit within enlarged portion of the syringe shield 411 that allows user access to the syringe 41 and plunger 422. The enlarged portion of the housing may further accommodate the piston or other part of the motor or pump that is configured to associate with the plunger 422 allowing the plunger to advance and retract.

Figure 4C:
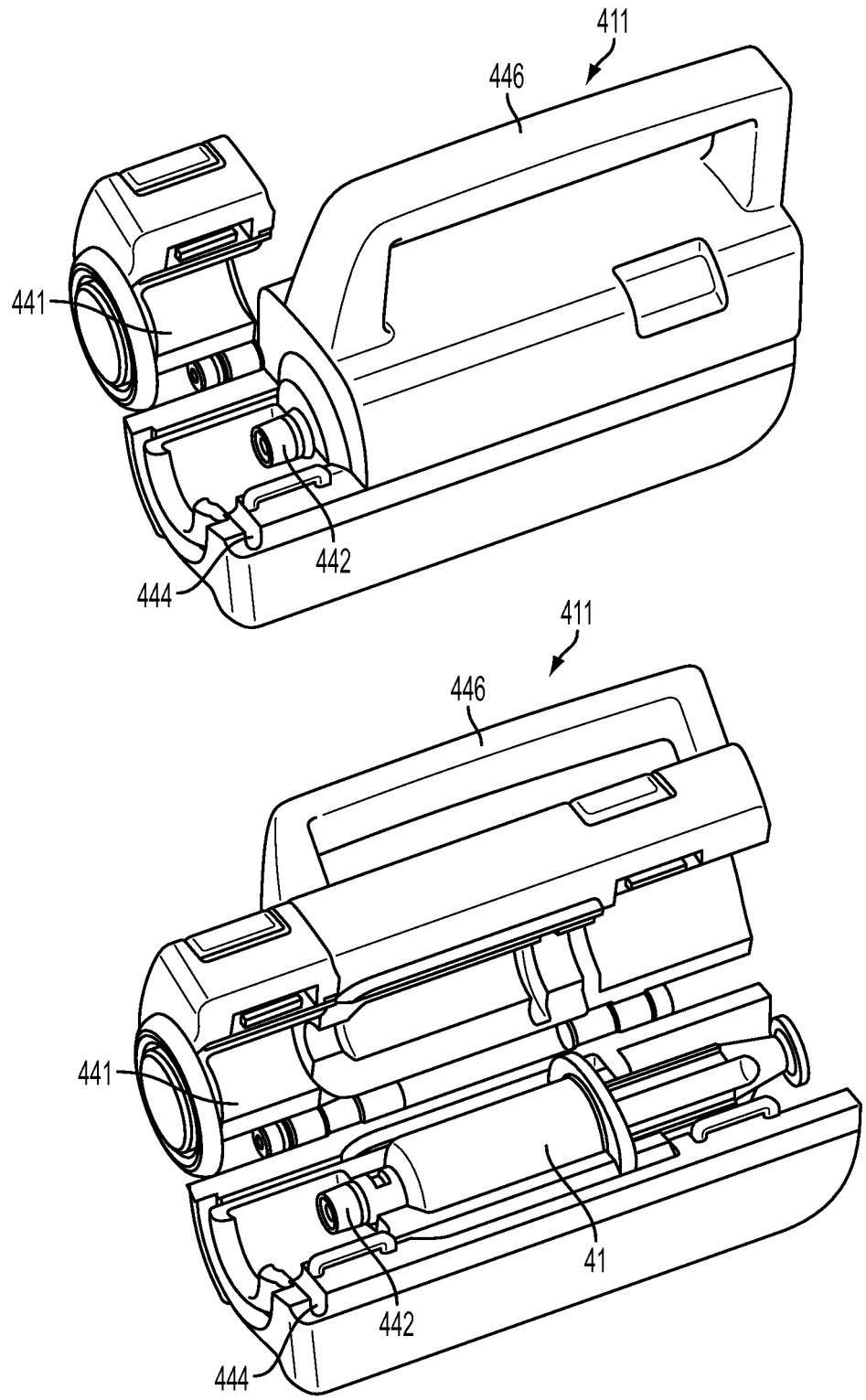
FIG. 4C is a drawing showing a syringe shield and a carrier handle.

In some embodiments, as illustrated in FIG. 4C the syringe shield may include a forward extension 441 designed to encase a connector portion 442 of the syringe 41 and a portion of the tubing extending from the connector 442 of the syringe 41 to a delivery device. The forward extension 441 may be connected to the syringe shield 411 and form part of the syringe shield 411. In some embodiments, the forward extension 441 may be separately attached to the syringe shield 411 and may include a separate hinged portion that allows access to the connector 442 and tubing section when the syringe 41 is encased in the syringe shield 411. In certain embodiments, the forward extension 441 may include a lateral exit port 444 through which the tubing section may exit the syringe shield 411. The forward portion of the forward extension 441 may be enclosed with a radiation blocking material to reduce shine from the connector 442 and potential exposure of the user to the radiation.

FIG. 4C additionally shows a syringe shield 411 having a built in handle 446. As illustrated, the handle 446 may be built in to or fixedly attached to at least a portion of the syringe shield 411. For example, the handle 446 may be fixedly attached to a hinged portion of the syringe shield that encases the syringe body and the aft extension.

The syringe bore 417 may be configured to accommodate any syringe or type of syringe known in art, and in some embodiments, the syringe bore 417 may provide a universal fitting for syringes of various types and sizes. For example, in particular embodiments, the syringe bore 417 may be configured to accommodate syringes having similar flange sizes and body lengths but different body diameters. Therefore, a syringe having a diameter sufficient to allow the syringe to hold 10 ml, 15 ml, 20 ml, or 30 ml and a syringe having a diameter sufficient to allow the syringe to hold 1 ml, 3 ml, or 5 ml can securely held within the syringe bore 417.

Figure 4D:
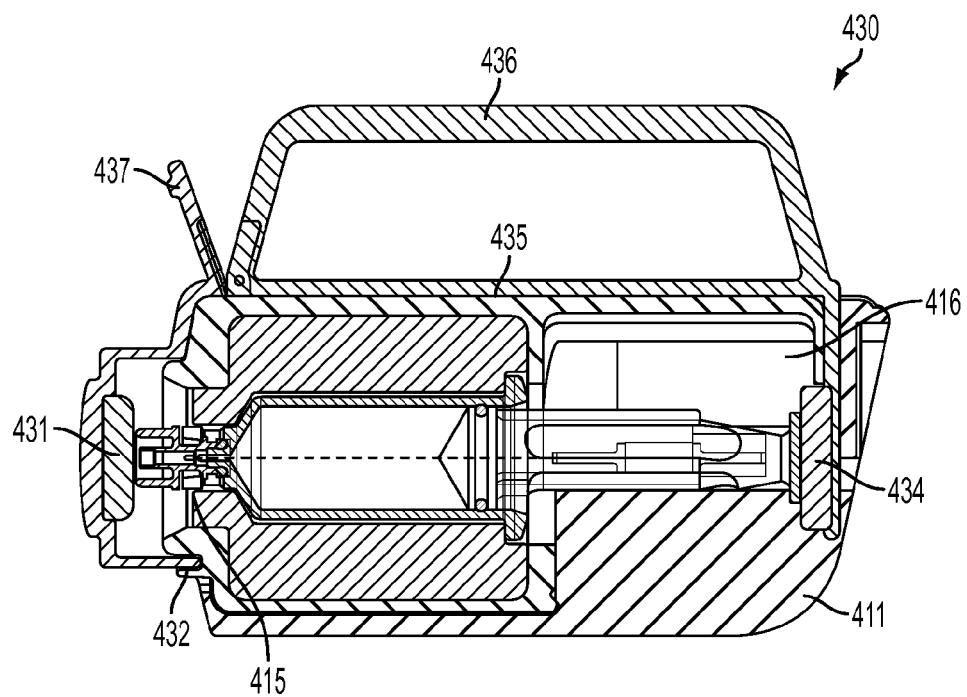
FIG. 4D is a drawing showing another embodiment of a syringe shield and carrier handle.
Figure 4D:
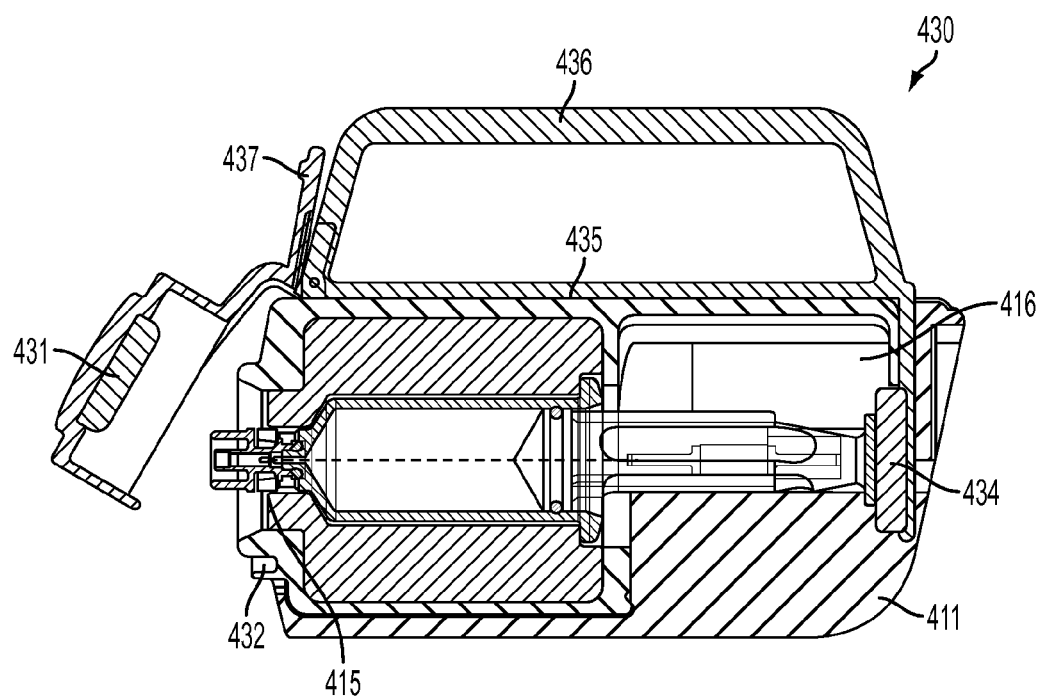

Further embodiments include a carrier handle 430 designed to attach to the syringe shield 411 to ease transport of the radiopharmaceutical and reduce exposure to the person carrying the syringe shield 411. For example, as illustrated in FIG. 4D, in some embodiments, a carrier handle 430 may include a tubing bore cover 431 configured and arranged to fit within the tubing bore 415 and/or a groove, flange, 432 or other attachment means associated with the tubing bore 415. The carrier handle may further include a plunger cover 434 configured and arranged to associate with the enlarged portion of the syringe housing 411 by, for example, contacting the housing 411 within the enlarged portion of the housing 411. In some embodiments, the tubing bore cover 431 and/or the plunger cover 434 may include a material capable of blocking radioactive emissions that is positioned to block emission that could otherwise escape through the tubing bore 415 and the plunger access point 416. In particular embodiments, carrier handle 430 may include a carrier body 435 that includes a grip portion 436 and the plunger cover 434. The tubing bore cover 431 may be hingedly attached to the carrier body and may include a lever or button 437 that is configured to allow the tubing bore cover to be released from the tubing bore 415 or corresponding flanges and grooves 432 on the syringe shield 411 when the lever or button is depressed.

In operation, the user may grasp the syringe shield 411 by positioning the plunger cover 434 within the plunger access point 416 or within the enlarged portion of the syringe shield 411 while the lever or button 437 is depressed. The tubing bore cover 431 may be positioned over the tubing bore 415 and the lever or button 437 can be released such that the tubing bore cover 431 is properly positioned within the tubing bore 415 and corresponding grooves 432. The carrier handle 430 is thereby sufficiently connected to the syringe shield to allow the user to easily pick up and transport the syringe shield 411 without actually touching the housing itself. To remove the carrier handle 430, the user can position the syringe shield 411 within the delivery injector body 11 to allow the syringe shield 411 to connect to the syringe mount 24. The lever or button 437 may be depressed releasing the tubing access bore cover 431 from the tubing access bore 415 and corresponding groove 432, and the user may rotate the carrier handle 430 such that the plunger cover 434 is removed from the plunger access point 416 and enlarged portion of the syringe shield 411. Finally, the carrier handle 430 can be withdrawn from the syringe shield 411 while the housing 411 remains mounted on the delivery injector body 11. Exposure to radioactive emissions from the radiopharmaceutical is minimized during transport, and only occurs during loading of the syringe 41 into the syringe shield 411 and installation of the tubing sections after the carrier handle 430 has been removed.

The carrier handle 430 and syringe shield 411 may be made from any material. For example, the carrier handle 430 and syringe shield 411 may be made from a metal, a polymeric material, or combinations thereof. In certain embodiments, the carrier handle 430 may be prepared from a rigid polymeric material such as a polycarbonate that may reduce the weight of the combined syringe shield 411 and the carrier handle 430, while the syringe shield 411 may be prepared from a metal or other material that is capable of blocking radioactive emissions such as tungsten or lead. In still other embodiments, the syringe shield 411 may be made from a metal such as tungsten or lead that is covered in a polymeric material such as a polycarbonate or light weight metal such as aluminum. In still other embodiments, the syringe shield 411 may include a pigment or dye that eliminates exposure of optical tracers to light. For example, in embodiments in which an optical tracer is delivered using the delivery device, the syringe shield 411 may be prepared exclusively from an opaque or colored material to absorb particular wavelengths of light to reduce decay of the optical tracer. In such embodiments, the syringe shield 411 may not include a metal or other material to block radioactive emissions, and the radioactive emissions blocking material 412 portion of the devices presented in FIG. 4 may be omitted and replaced with, for example, a polymeric material.

Certain embodiments are directed to methods for calibrating a piston syringe drive system such as the radiopharmaceutical delivery system 10 described above. In some embodiments, a motor driven piston may be used to contact a syringe, and in particular embodiments, the piston may include one or more switches on the face of the piston configured to contact the plunger. At least one switch may have travel that is beyond the activation point providing a large amount of overtravel to allow for high plunger "search" speeds. Such a piston driven motor may be operated by methods including the steps such as loading a syringe with a composition. An empty syringe may be loaded into the device with the plunger at any position. The piston may be advanced at a high speed until a switch on the face of the piston is activated against the plunger. The switch will travel beyond its activation point after the piston has contacted the plunger. The piston may then be retracted at a very slow speed until the switch is deactivated. These steps allow for determination of the switch activation/deactivation position. The control system may then record and store the deactivation position. These steps may be repeated two or more times, and the average deactivation position can be calculated from these data points and stored in memory. In still other embodiments, sensors such as laser or other optical, magnetic sensors, or ultrasonic sensors may be used to detect the plunger and position the piston to allow for proper dispersion of the radiopharmaceutical or optical agent.

In operation, a syringe can be loaded with any amount of a composition and the syringe may be installed into the injector. The syringe may be loaded with any amount of the composition and the plunger may be in any position allowing the user to fill the syringe to any desired volume. The piston may then be advanced at high speed until it contacts the plunger and actuates the switch. The piston will travel beyond the switch activation point due to inertial effects and signal or computer lag time. Using the average activation/deactivation point calculated during the calibration routine and the distance from the end of the switch trigger to the activation point, the position of the end of the plunger can be determined. The volume of the composition in the syringe can then be determined based on the position of the plunger and the diameter/type of syringe introduced into the system, which can be inputted by the user or detected based on marking on the syringe that can be read by the system.

The radiopharmaceutical delivery system 10 of various embodiments as exemplified in FIG. 5 may further include a delivery tubing set 50 for transferring the radiopharmaceutical from the syringe 51 to a delivery port 52 configured to allow injection of the radiopharmaceutical into a subject. The delivery tubing set 50 may include a tubing extension 53 of any length extending from a syringe connector 54 and the delivery port 52, and in some embodiments, the tubing may include intervening tubing sections 53b that act as extensions or perform specialized functions as discussed below. The tubing extension 53 may generally be of sufficient length to extend from the syringe to the subject to whom the radiopharmaceutical is to be delivered, and in some embodiments, the tubing extension 53 may be of sufficient length to be inserted into a tubing management system as described above (see FIG. 3). Thus, the tubing extension 53 may have length of from about 5 in to about 50 in, and in particular embodiments, the tubing extension 53 may have a length of from about 10 in to about 50 in, about 15 in to about 45 in about 20 in to about 40 in, or about 20 in to about 35 in. In certain embodiments, the tubing extension 53 may have a length of 20 in, 36 in, or 48 in. Tubing extensions of such lengths may be configured to be accepted by a tubing management system while providing sufficient length to allow user maneuverability during the radiopharmaceutical delivery procedure.

The tubing extensions 53 of various embodiments may include one or more connectors on each end, and the connector may be any connector known in the art. For example, the syringe connector 54 may be mounted on an end of the tubing extension configured to be attached to the syringe and may be, for example, a luer or swabable luer type connector. The end of the tubing extension 53 opposite the syringe connector 54 may be configured to attach to a needle or other delivery device and may be a luer or swabable luer type connector. In other embodiments, the end of the tubing extension 53 opposite the syringe connector 54 may be configured as a tubing connector 55 as illustrated in FIG. 5 such that the tubing connector may attach to intervening tubing sections 53*b*. In various embodiments, the tubing connector may be a luer connector.

Figure 27:
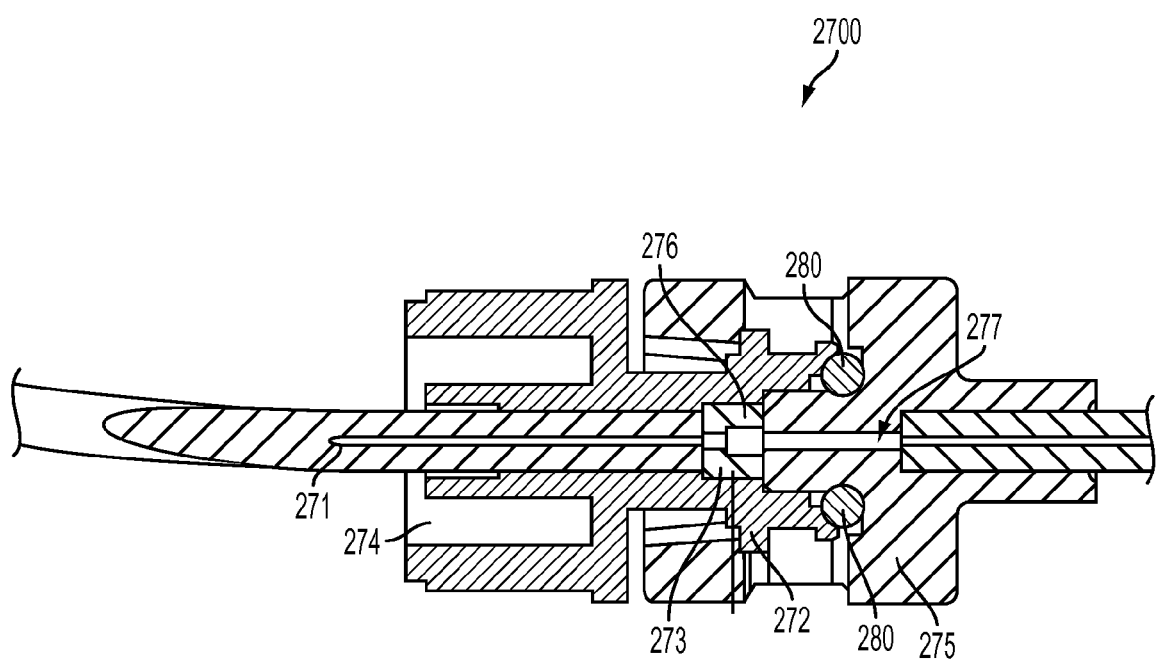
FIG. 27 is a drawing of a connector as described in embodiments of the invention.

In other embodiments, a compressible sealing connector may be used. As illustrated in FIG. 27, such sealing connectors 2700 may have a generally cylindrical in shape and dimensioned to be concentric with the conduit or tubing 271 of the connector. A distal end 272 of sealing element can, for example, be flush with the distal end of conduit or tubing 273 or extend beyond the distal end of conduit or tubing with a hole aligned with the ID of the tubing. In either case, the base of distal end 272 of sealing element can be shaped, for example, tapered, to generally match the inside surface of the second cooperating connector, with which it comes into contact upon connection of first cooperating connector 274 and second cooperating connector 275. The tapered section provides a sealing surface between surface of second cooperating connector 274 and sealing element 276. Connection of first cooperating connector 274 and second cooperating connector 275 causes compression of sealing element 276 to effect a seal. In other embodiments, sealing can occur at an O-ring 280 between the first cooperating connector 274 and second cooperating connector 275. Because an O-ring 280 effects the seal between cooperating connectors, 274, 275, no taper is necessary. Therefore, in certain embodiments, the inner surface of the sealing connector can be cylindrical and not tapered. In particular embodiments, sealing connectors, including sealing connectors having a tapered or O-ring sealing mechanism, may be attached to one another using a threaded attachment means and in certain embodiments, a threaded quarter-turn attachment method may be used.

As compared to standard luer-type connectors, in the devices and systems of the present invention, the distal end or exit of conduit or tubing 273 is positioned more closely to a flow path opening of second cooperating connector 275, thereby reducing potential lost volume. Alternatively, extending a sealing element 276 beyond the end of conduit or tubing 271 and matching the dimension of a passage within sealing element 276 to passage 277 can virtually eliminate such potential lost volume. The interconnection between second cooperating connector 275 and the downstream fluid path element attached thereto is also designed to reduce or eliminate sharp flow transitions (which can, for example, damage cells and/or other fluid components being administered). Sharp transitions can, for example, occur between connection of any two fluid path elements or internally within a particular fluid path element. Such connectors are more fully described in U.S. Publication No. 2010/0063481, which is hereby incorporated by reference in its entirety. In embodiments, having an O-ring 280 that effects the seal between cooperating connectors, lost volume is nearly completely eliminated. Without wishing to be bound by theory eliminating lost volume may provide a further improvement of the accuracy of the device by reducing the potential for the injected pharmaceutical to be trapped in the lost volume and not dispensed to the subject.

In some embodiments, the tubing extension 53 may be configured to connect to a needle or other deliver device directly, and such needles or other delivery devices may be known and commercially available. In other embodiments such as those illustrated in FIGS. 6A and 6D the tubing extension may be configured to connect to a needle or other delivery device and may include a needle 61*a*, 61*b*, having a needle handle 62*a*, 62*b* configured to be grasped by the user during insertion of the needle into the subject. In some embodiments, the needle 61*a*, 61*b* may include a needle cover 67*a*, 67*b* configured to cover the needle prior to insertion into the subject.

Figure 6A:
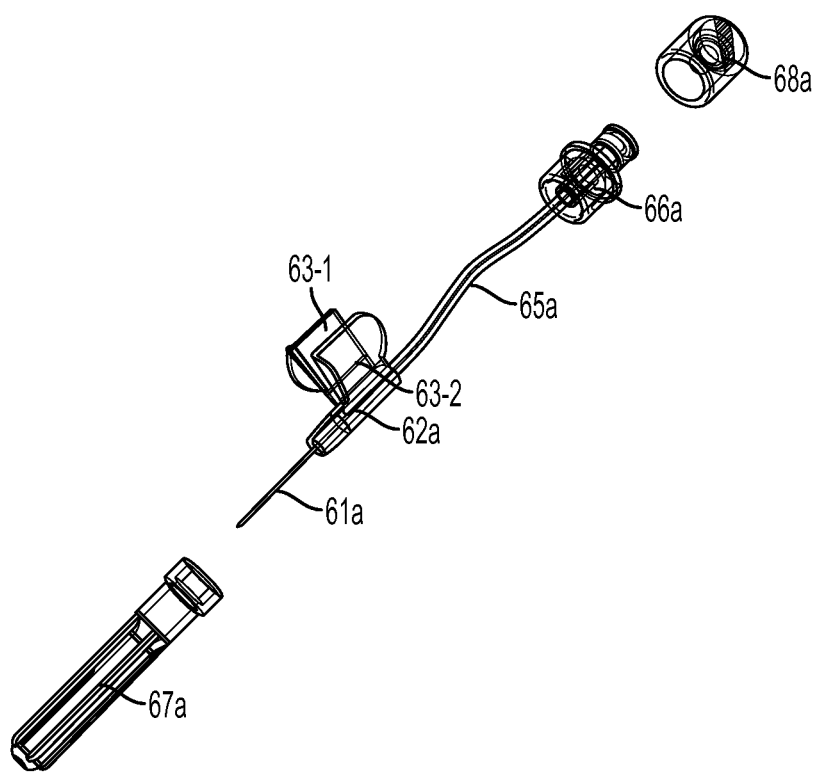
FIG. 6A is a drawing showing a needle and tubing with a winged needle handle.

The needle handle 62*a*, 62*b* may be of any design or configuration. For example, in some embodiments as illustrated in FIG. 6A, the needle handle 62*a* may have a winged configuration such that a pair of removable wings 63-1, 63-2 can be brought into contact with one another during insertion of the needle, such that the user can simultaneously grasp both wings 63-1, 63-2. The wings 63-1, 63-2 may then be spread following insertion of the needle to provide a larger surface area for contact with the subject and to improve stability when the needle is attached to the subject using, for example, medical tape. The wings 63-1, 63-2 may be freely movable and mounted to the needle 61*a* using flexible plastic, and in other embodiments, the wings 63-1, 63-2 may be attached to one another such that a connector must be broken to allow the wings to be spread. In other embodiments, the wings may be separated breaking the needle handle 62*a* from the needle 61*a* and tubing section 65*a*.

Figure 6B:
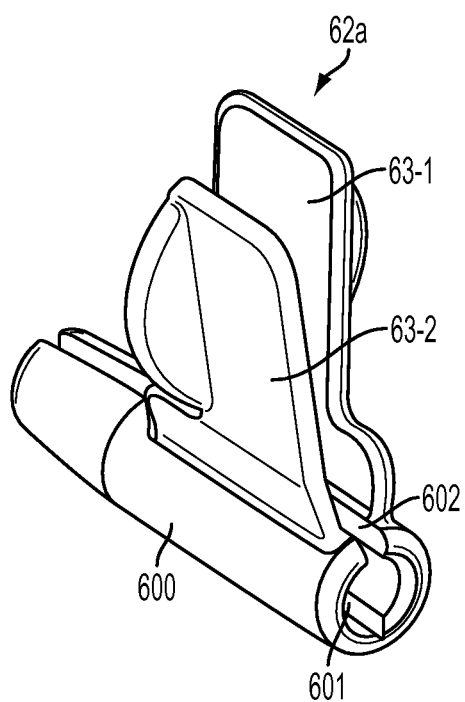
FIG. 6B is a drawing showing a winged needle handle.

In some embodiments, the needle handle 62*a* may be designed to be easily removed by the user. As illustrated in FIG. 6B, the needle handle 62*a* may include a needle handle body 600 and a pair of offset wings 63-1 and 63-2. The offset wings may be positioned such that the wings can be separately grasped by the user and pulled in opposite directions. The needle handle 62*a* may further include a separation 602 on the surface corresponding to the wings 63-1 and 63-2 and a cleft 601 on the opposite surface of the needle handle body 600. The separation 602 and the cleft 601 may allow for the user to crack separate the wings 63-1 and 63-2 through the separation 602 allowing the needle handle 62*a* to break along the cleft 601 into two pieces. The pieces may be easily removed from the needle 61*a* and tubing section 65*a*. In addition, the cleft 601 and the separation 602 allow the needle handle 62*a* to tighten around the tubing 65*a* when the wings 63-1, 63-2 are squeezed together preventing movement as the needle is inserted into the subject.

Figure 6C:
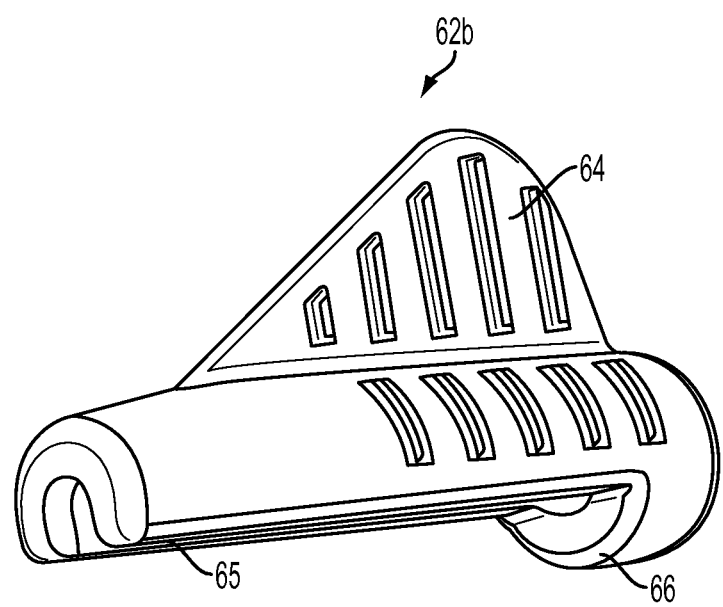
FIG. 6C is a drawing showing a needle and tubing with a fin needle handle.

In other embodiments, as illustrated in FIG. 6C, needle handle 62*b* may be a single wing or fin 64 associated with the needle 61*b*. In use, the user may grasp the wing or fin 64 during insertion of the needle 61*b* and then rotate the needle 61*b* and wing or fin 64 such that it contacts the subject and can be secured to the subject using, for example, medical tape. In still further embodiments, either the wings 63-1, 63-2 or the single wing or fin 64 may be configured to be removed after insertion of the needle into the subject. In such embodiments, the wings 63-1, 63-2 or single wing or fin 64 may be attached to the needle with a breakable connector and the user may simply break these handles from the tubing or needle.

As illustrated in FIG. 6C, in some embodiments, the needle handle may have a fin 64 shape. As in the above embodiments, in such embodiments, the tubing extension may include a needle operably connected to a tubing section. The needle handle 62b may have a fin shape 64 that is sized and shaped to be grasped by the user during insertion of the needle into the subject. In some embodiments, a portion of the needle handle opposite the fin 64 may be removed. For example, as illustrated in FIG. 6C, the needle handle 62b may include a c-shaped bore 65 sized to accommodate the tubing section such that a portion of the tubing section is exposed through the needle handle. In some embodiments, the exposed portion of the tubing section may be opposite the fin 64 as depicted, and in other embodiments, the fin 64 may be offset from the exposed portion of the c-shaped bore 65 to ease handling. In use, the c-shaped bore 65 may allow the tubing section and, by extension, the needle to contact the subject at a lower angle relative to the subject's skin allowing the needle to by introduced into blood vessels near the surface of the skin. In some embodiments, a portion of the tubing section may be encased in the needle handle 62b by a ventral enclosure 66, and the ventral enclosure 66 may be positioned at the distal end of the needle handle 62b.

Figure 6D:
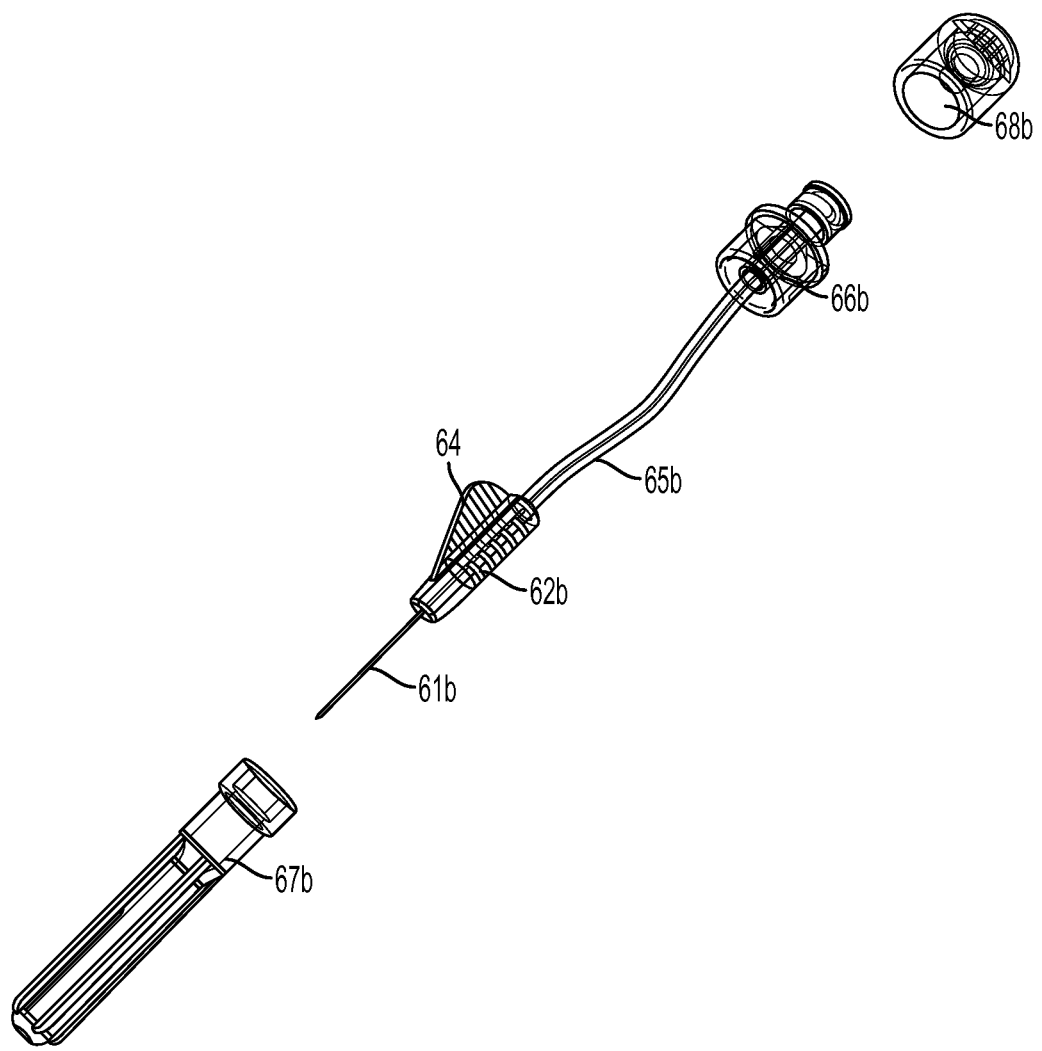
FIG. 6D is a drawing showing a needle and tubing with a fin needle handle.

In some embodiments, as illustrated in FIG. 6D, the needle 61a, 61b may be directly attached to a connector configured to allow the needle to be attached to another tubing section. In other embodiments, the needle 61a, 61b may be attached to a needle tubing section 65a, 65b which is then attached to a connector 66a, 66b. The needle tubing section may be of any length and, generally, may be of a length sufficient to allow the user to easily manipulate the needle 61a, 61b and needle handles 62a, 62b without interference from the connector 66a, 66b. Thus, the needle tubing section 65a, 65b may have a length of from about 0.5 in to about 5 in, or in other embodiments, about 1 in, about 2 in, about 3 in, about 4 in, about 5 in, or any length between these exemplary lengths.

Figure 6E:
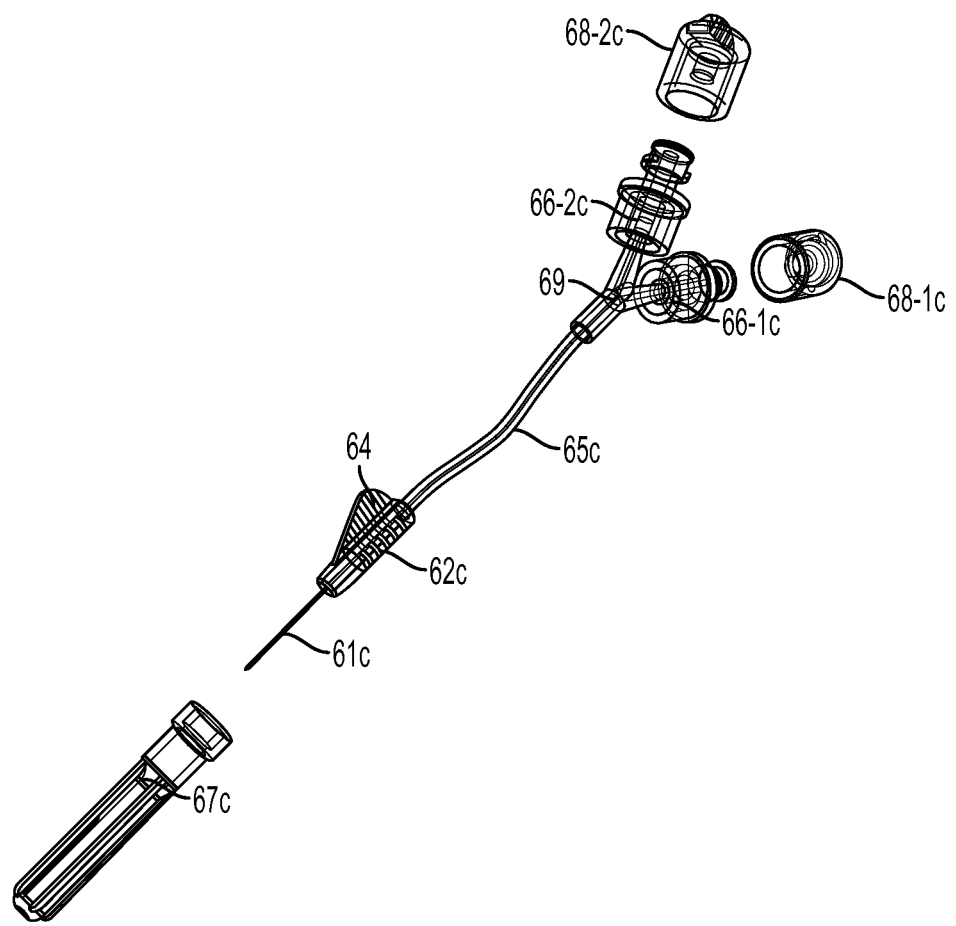
FIG. 6E is a drawing showing a needle and tubing with a fin needle handle and a Y-connector.

The connector 66a, 66b associated with the needle tubing section 65a, 65b may be any type of connector known in the art such as, for example, a luer type connector. In certain embodiments, the connectors may be associated with a Y-connector 69 as illustrated in FIG. 6E. The Y-connector 69 may be attached directly to the needle 61c and needle tubing section 65c, or in other embodiments, the Y-connector 69 may be attached to the needle 61c and needle tubing section 65c through an additional connector (not shown). On the end opposite the needle 61c or needle tubing section 65c, the Y-connector may terminate in two or more connectors 66-1c, 66-2c, and each connector can be any type or connector known in the art. In some embodiments, the two or more connectors may be different types of connectors. For example, in particular embodiments, one connector may be adapted to accommodate a needle allowing for manual delivery or a composition to the subject during the radiopharmaceutical delivery procedure, and the other connector may be a tubing connector.

In some embodiments, the needle connector may include a needle tube connector cap 68a, 68b, 68-1c, 68-2c configured to cover the connector prior to insertion of the needle 61a, 61b, 61c into the subject.

Figure 7A:
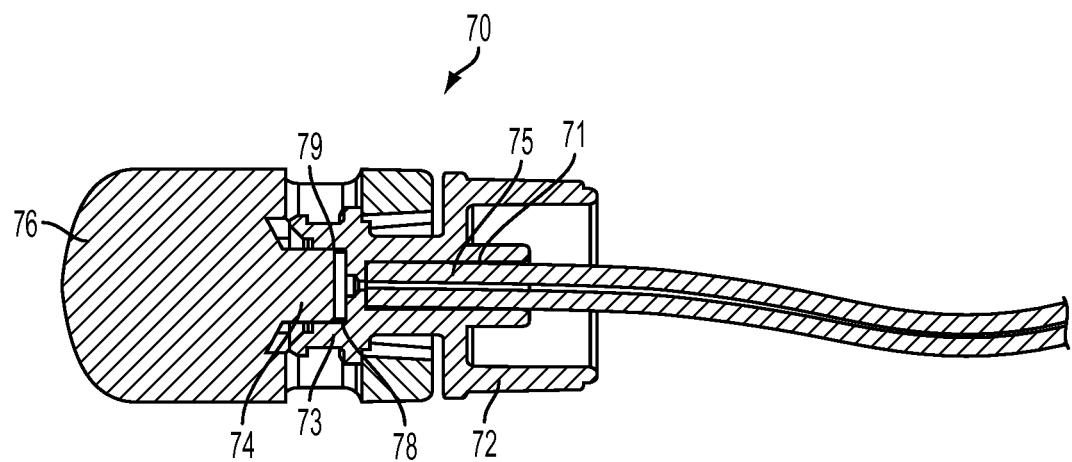
FIG. 7A is a drawing showing a primer cap.

In some embodiments, the needle connector 66a, 66b, 66-1c, or 66-2c may include a primer cap 70. FIG. 7A shows a cross sectional view of a primer cap 70. The primer cap 70 may, generally, include a tubing connector designed to connect to a tubing section, and a cap designed to removably connect to the tubing connector. The tubing connector may include a first fitting 71 for connecting to the needle tubing section 65a, 65b, and 65c. The first fitting 71 may be a pressure fitting, a connector such as a luer connector, or the compressible sealing connector described above, and may be physically attached to the needle tube by physical means such as soldering or glue. The primer cap may further include a nut 72 designed and configured to be grasped by the user when the primer cap 70 is connected to or disconnected from the needle connector 66a, 66b, 66-1c, 66-2c. In some embodiments, the primer cap may further include an extension 73, such as a female luer fitting, opposite the first fitting 71 for connecting to another connector. The primer cap 70 may generally include a bore 75 extending from the first fitting 71 through the nut 72 allowing for free flow of fluid between the first fitting 71 and through the nut 72.

The cap 76 may include a handle designed to be grasped by the user. The cap 76 may generally be configured to extend away from the first fitting 71. In some embodiments, the cap 76 may include a plug 74 that is configured to create an airtight seal within the sealing bore 79 of the extension 73 via a sealing lip 78, which may be pliable to allow compression. In other embodiments, the plug 74 may be configured to create the airtight seal on the outside of the extension 73. In yet other embodiments, the cap 76 may include a plug insert in addition to or in place of the sealing lip 78 shown in FIG. 7A. In such embodiments, the plug insert may be designed and configured to be inserted into the sealing bore 79 of the primer cap 70 and substantially fill and create an airtight seal within the bore. In some embodiments, the sealing lip 78 may be a sealing device such as an O-ring or the like to effectuate a seal.

Figure 7B:
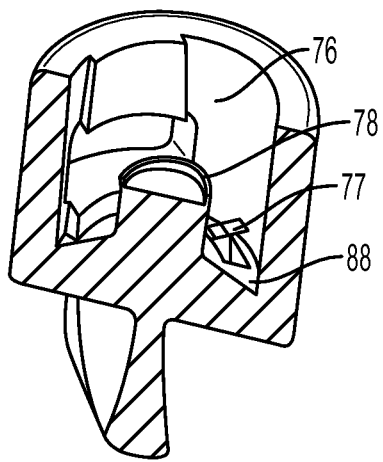
FIG. 7B is a drawing showing a primer cap.

In some embodiments, the cap 76 may include a means for producing a spring washer effect using, for example, an o-ring disposed within a groove on a surface of the cap 76 surrounding the sealing lip 78. In other embodiments, as illustrated in FIG. 7B, the cap 76 may include one or more cantilever tabs 77 protruding into a groove 88 on a surface of the cap 76 surrounding the sealing lip 78. In use, the cantilever tabs 77 may be compressed when the cap 76 is attached to the tubing connector to provide a spring washer effect.

In operation, primer cap 70 may be operably connected to needle 61a, 61b, 61c, needle tubing section 65a, 65b, 65c, or a terminus of the Y-connector 69. The needle may be inserted into subject while the airtight seal created by the plug 74 in the sealing bore 79 of extension 73 reduces or eliminates the flow of blood or other fluid into the needle 61a, 61b, 61c, needle tubing section 65a, 65b, 65c, or Y-connector 69. The user may then grasp handle 76 and remove the cap creating a vacuum within the bore of connector 73 drawing blood or other fluids from the subject into the needle 61a, 61b, 61c, and needle tubing section 65a, 65b, 65c. A wet-wet connection can then be made with tubing coming from the delivery system and the delivery protocol can be carried out.

In certain embodiments, the sealing bore 79 of extension 73 may be configured to allow a particular amount of blood or other fluid into the device. For example, in some embodiments, the bore may have substantially the same volume as the volume of the needle 61a, 61b, 61c, needle tubing section 65a, 65b, 65c, and Y-connector 69, where applicable. Thus, when the plug 74 is removed, a volume of blood equal to the volume of the needle 61a, 61b, 61c, needle tubing section 65a, 65b, 65c, and Y-connector 69 is drawn into the device. In other embodiments, the volume of the bore 79 may be greater than or less than the volume of the needle 61a, 61b, 61c, needle tubing section 65a, 65b, 65c, and Y-connector 69.

Figure 5A:
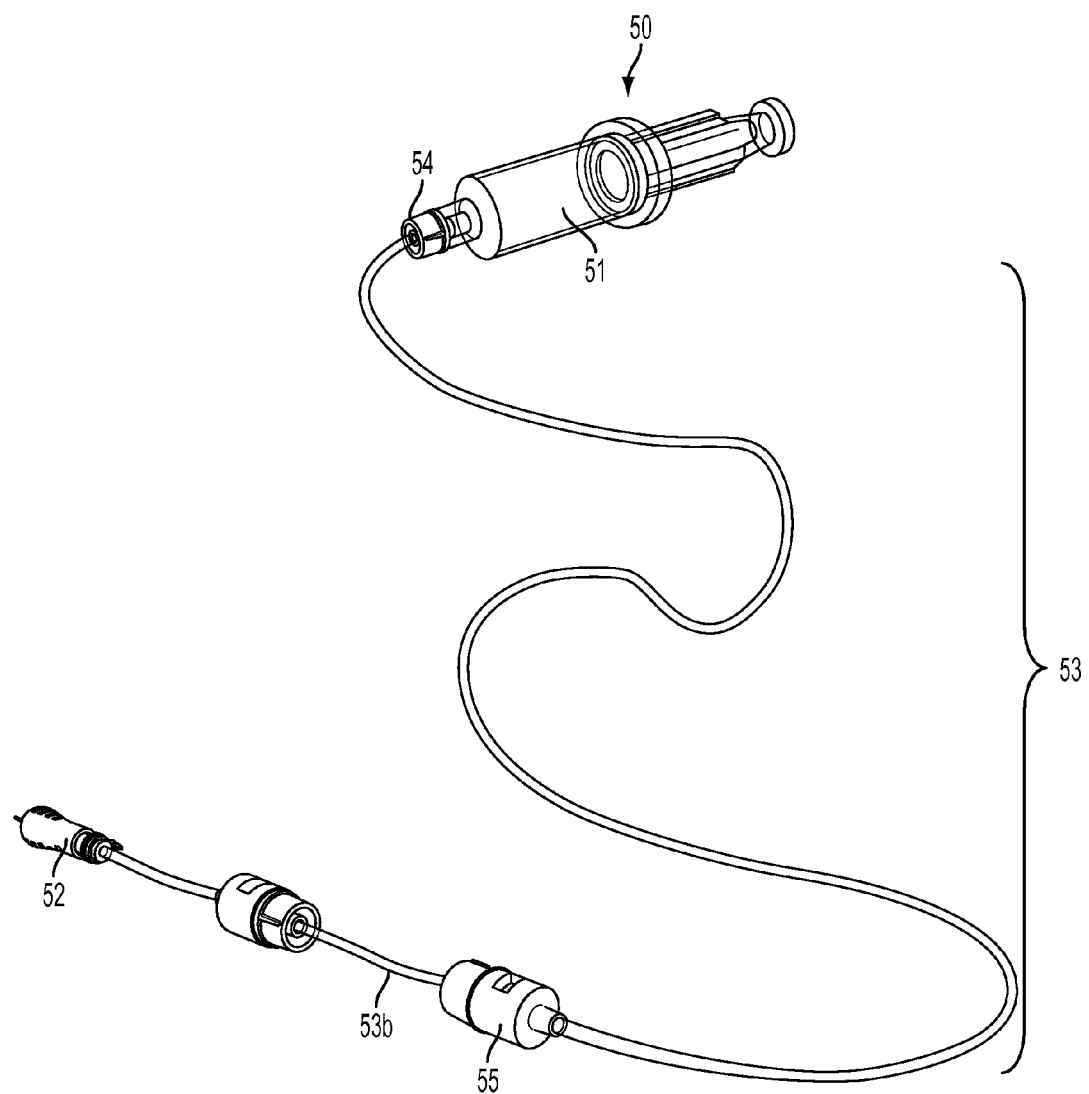
FIG. 5A is a drawing showing a tube extension and the various features thereof.

With reference to FIG. 5A, the tubing extension 53 may include any number of additional tubing sections 53b having any length, and additional tubing sections 53b may be incorporated into the tube set 50 for any reason. For example, in some embodiments, additional tubing sections may be added to elongate the tube set 50 making it suitable for the administration of radiopharmaceuticals at a greater distance, e.g., opposite a wall or radiation shield housing a radiopharmaceutical delivery device 11, or to provide improved maneuverability for subjects of various sizes, e.g., a longer tube sets may be necessary for delivery to larger animals such as dogs, horses, cows, pigs, monkeys, or humans compared to a mouse, which may be placed on a table near the delivery device 11.

In certain embodiments, an additional tubing section 53*b* may be provided as a diffusion chamber and may provide a means of monitoring diffusion and avoiding mixing of the radiopharmaceutical with blood or other fluids from the subject. In such embodiments, the diffusion chamber may include a length of tubing of about 1 in to about 5 in in length that may be clear or tinted to allow the user to visually observe movement of blood toward the tubing extension 53. The diffusion chamber prevents blood or body fluid from reaching connector 55 preventing contamination of extension 53. In operation when blood or other bodily fluid reaches the connector between the diffusion chamber 53*b* and the tubing extension 53 or nears the connector, the diffusion chamber may be replaced to eliminate potential contamination of the radiopharmaceutical in the tubing extension 53. At the same time, the needle 61*a*, 61*b*, 61*c* and needle tubing section 65*a*, 65*b*, 65*c* can be changed for each subject to avoid contamination at the needle.

Figure 5B:
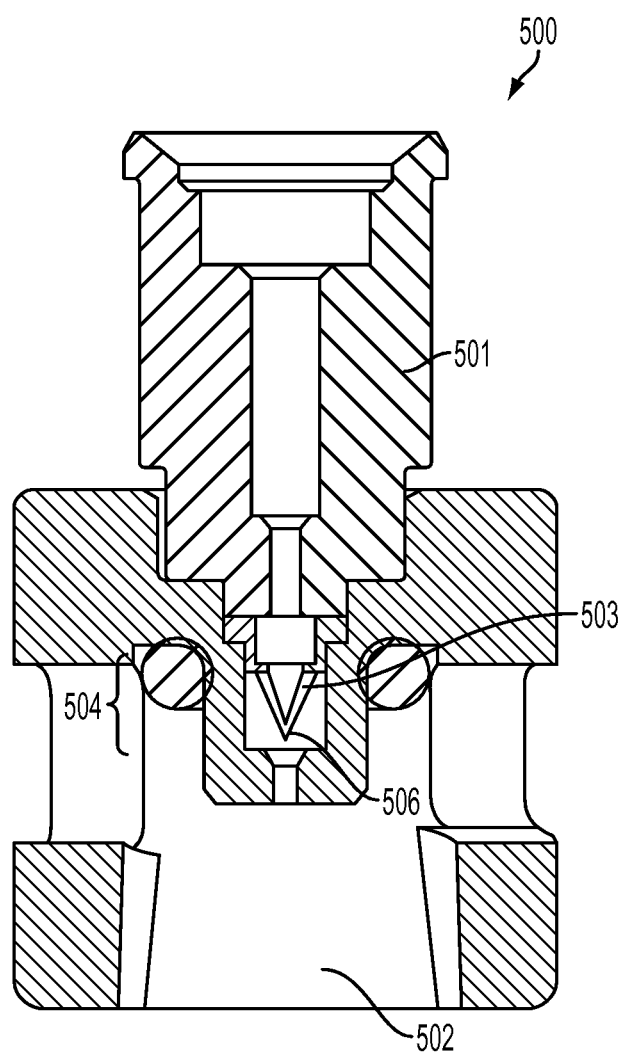
FIG. 5B is a drawing showing a connector containing a check valve.

Further embodiments are directed to a tubing connector having an internal check valve which can operate to reduce contamination. For example, FIG. 5B shows a check valve 504 disposed within a tubing connector 500. In this example, the closing member 503 is disposed at the end of a male component 501 of the connector 500, and this closing member 503 fits within a check valve bore 506 in the female component 502 of the tubing connector 500. In other embodiments, the check valve including both a closing member and a check valve bore may be completely disposed within either the male or female component. The check valve in such embodiments may be configured to allow fluid to flow toward the subject, but stop fluid from flowing back into the delivery tubing. Thus, in FIG. 5B fluid would flow from the male component 501 through the female component 502 and to the subject. The diffusion into the delivery tubing is reduced or eliminated.

Additional embodiments include small bore tubing having thick outer walls that allow for ease of handling and/or assembly. For example, the tubing of various embodiments may having an inner diameter for from about 0.25 mm to about 1 mm or any diameter encompassed by this range including but not limited to 0.25 mm, 0.5 mm, 0.8 mm, and 1 mm. The outer diameter of such tubing may be up to about 1 inch. For example, in some embodiments, the outer diameter of the tubing may be from about 0.05 in to about 1 inch, about 0.1 in to about 0.75 in, about 0.25 inch to about 0.5 in or any diameter encompassed by these ranges, and in certain embodiments, the outer diameter of the tubing may be 0.25 in, 0.5 in, or 0.75 in. The tubing of such embodiments may be composed of any material known in the art that is used to make tubing, and in particular, embodiments, the tubing may be composed of a flexible material. Thus, the tubing of various embodiments may be composed of a polymeric material such as, for example, polyvinyl chloride (PVC), polyethylene teraphthlalate (PET), fluorinated ethylene propylene (FEP), polytetraflourineethylene (PTFE), polyether etherketone (PEEK), polypropylene, polyethylene, thermoplastic elastomers, and the like.

The radiopharmaceutical delivery system 10 of some embodiments may further include additional shielding devices that are designed to envelop, cover, or otherwise contain radioactive emissions from the radiopharmaceutical while the radiopharmaceutical is in the extension tube. For example, the tube management system may allow the extension to be retracted into the delivery injector body 11 when radiopharmaceutical delivery is not taking place. Other embodiments of the system include a shielded mat 80 that can be placed on a work surface to prevent radioactive emissions from contacting a user through the work surface. In still other embodiments, one or more tube covers 81 may be placed over unshielded tubing to block emission from the radiopharmaceutical when the tube is one the work surface. In some embodiments, a single tube cover may be designed to cover a large portion of the extension tubing. For example, a single tube cover may be from about 2 in to about 5 in shorter than the length of the extension tube minus the length of extension contained in the tubing management system thereby reducing the overall emissions capable of contacting the user while providing sufficient external tubing to allow the user to maneuver the extension tube 53 during insertion of the needle and delivery of the radiopharmaceutical. Such a single tube cover may be straight or curved, and in some embodiments, the single tube cover may be bendable. The shielded mat 80 and tube covers 84 may be made entirely or partially from tungsten, lead, or other radioactive shielding materials.

Figure 8:
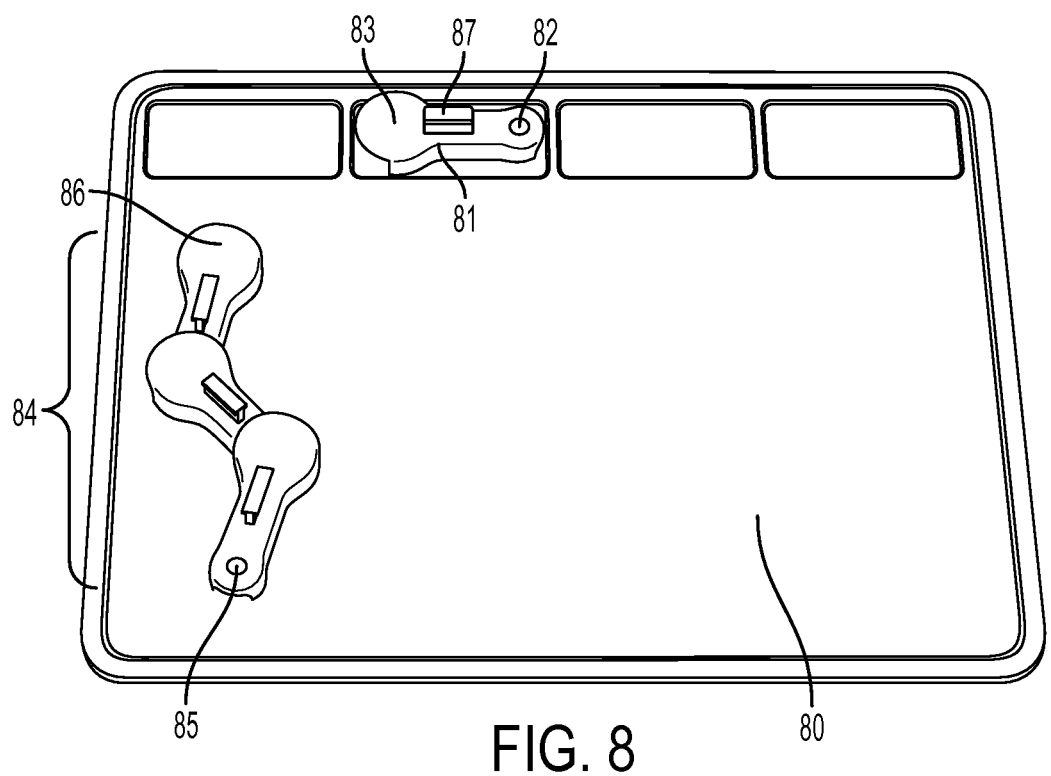
FIG. 8 is a drawing showing a shielded mat and tubing covers.

In other embodiments, the tubing cover may include a number of tube covers that are designed to be interlocking, allowing for a large array of different shapes and lengths using the same tubing covers. For example, as illustrated in FIG. 8, a plurality of short, single tube covers 81 may be combined by interlocking a first end 82 of the tube cover and a second end 83 of a neighboring tube cover. In FIG. 8, three single tube covers 84 are shown in interlocking configuration with the first end having a narrow character 82 contacted by a second end having a bulbous character 83. The tube covers of such embodiments, may be open on the lower portion such that outer walls of the tube cover contact the work surface, and the first end 82 and the second end 83 may be open to allow the extension tube to travel through the interlocked tube covers 84 unimpeded. In some embodiments, the first end may include an upper dimple 85 that is configured to contact a knob protruding from the lower surface of the second end 86 thereby allowing the user to move the interlocked tube covers 84 while the individual tube covers remain in contact with one another. The tube covers may further include additional features that facilitate handling such as, for example, handles 87, tube retainers, latches, and the like.

Figure 9:
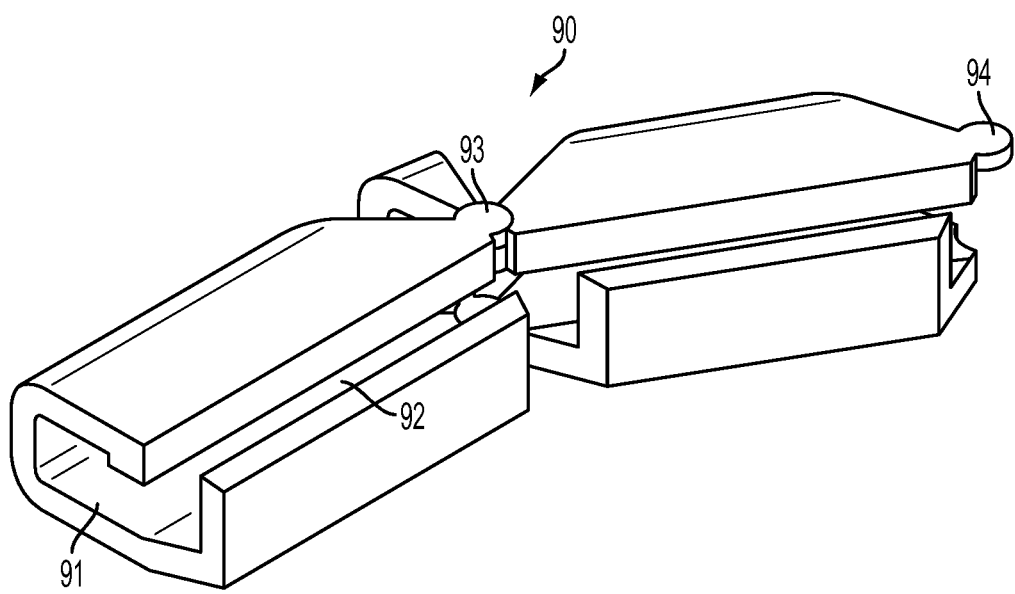
FIG. 9 is a drawing showing an embodiment of a tubing cover.

In further embodiments, the tube cover or tube covers may be configured to encase the extension tube. For example, as illustrated in FIG. 9, in some embodiments a tube cover 90 may include an internal channel 91 configured to accept the extension tube 53, and an insertion gap 92 configured to allow the extension tube 53 to be passed into the channel 91 by the user during use. As above, tube covers 90 having an internal channel 91 may include interlocking mechanisms 94 that allow individual tube covers 90 to be interlocked and connected to one another. Such tubing covers 90 may further include pivot joints 93 that allow bending of the tube while maintaining cover over the tubing, and other features, such as handles, latches, and the like to ease in handling.

In some embodiments, the system 10 may include one or more additional components including, but are not limited to, pinch valves, air detectors, and mounts or retainers for holding the connector ends of the delivery tube section, and the like and combinations thereof. The fluid delivery system 10 may include one or more pumping mechanisms configured to facilitate the movement of liquids through the system. Any suitable type of pumping mechanism can be used including, but not limited to, piston-driven syringe pumps, gear pumps, rotary pumps, in-line pumps, and peristaltic pumps. The system of various embodiments may include any number of cords for powering the system using standard AC outlets, and in some embodiments, the system may include a battery configured to power the system controller in the event that the system 10 is disconnected from an AC power source. In some embodiments, the system battery may be charged while the system 10 is connected to an AC power source.

Figure 10:
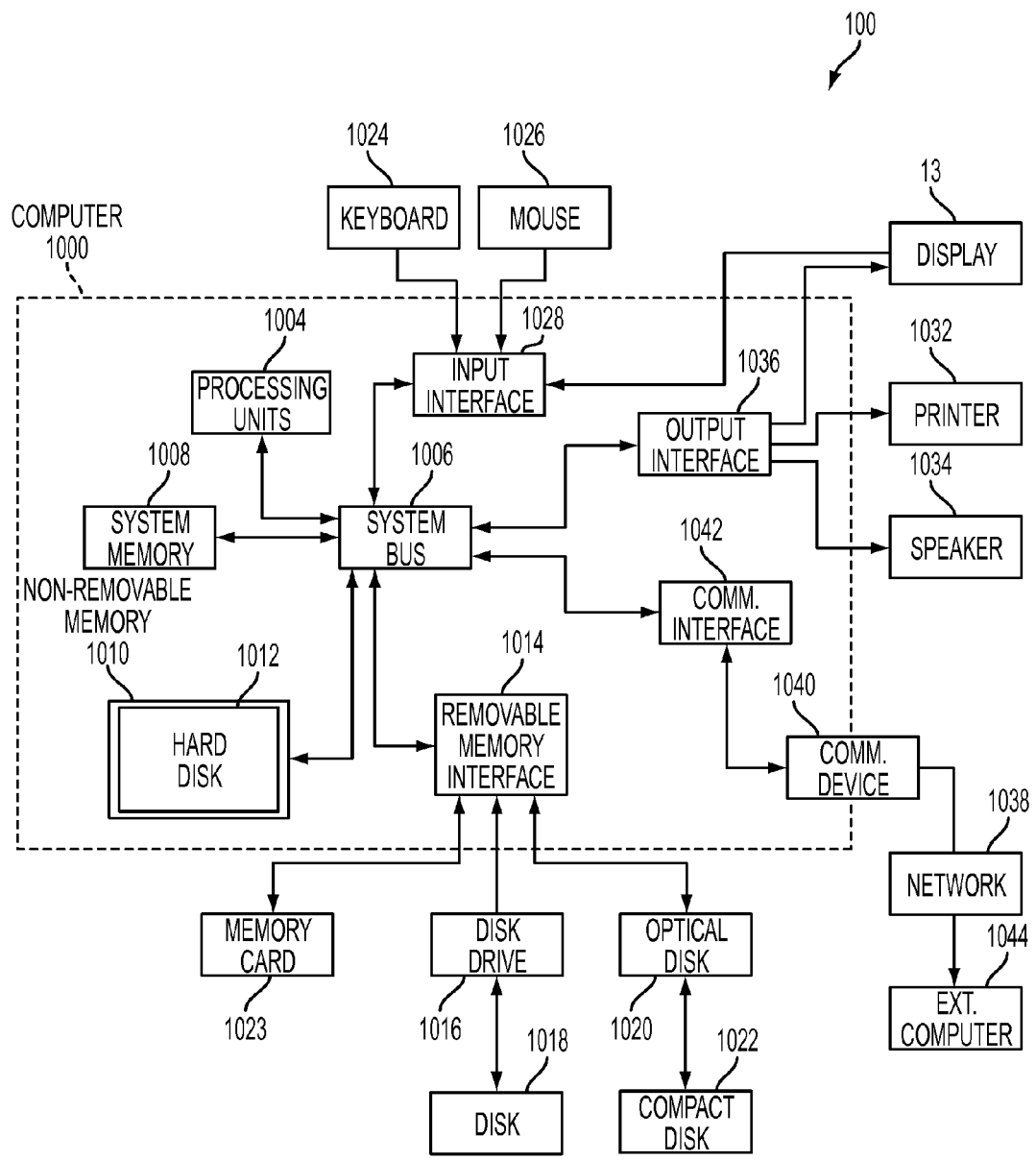
FIG. 10 is a schematic of a control system that can be incorporated into the system of the invention.

In various embodiments, the delivery system 10 may include a control system 100 (schematically represented in FIG. 10) in communication with the various components of the delivery system 10, including, for example, the display 13, pumps, motors, buttons, air detectors, printers, valves, stopcocks, and the like for controlling the operation of the system 10.

The control system 100 may include, but is not limited to, at least one computer 1000 having certain components for appropriate operation, execution of code, and creation and communication of data. The computer 1000 includes one or more processing units 1004 (typically referred to as a central processing unit or CPU) that serves to execute computer-based instructions received in the appropriate data form and format. Further, this processing unit 1004 may be in the form of multiple processors executing code in series, in parallel, or in any other manner for appropriate implementation of the computer-based instructions. As used herein, the computer 1000 may be operably configured to execute appropriate software to perform and implement the processing steps of the methods and systems disclosed herein. The system may include one or more computers 1000 or similar computing devices having a computer-readable storage medium capable of storing computer-readable program code or instructions that cause the processing unit 1004 to execute, configure, or otherwise implement the methods, processes, and transformational data manipulations discussed herein. Still further, the computer 1000 may be in the form of a personal computer coupled to the delivery system 10, a processor formed integrally with the delivery system 10, a computer provided remotely from the delivery system 10, or any other type of computing device having the necessary processing hardware to appropriately process data to effectively implement the presently-invented computer-implemented method and system, for example computer tablets and smart phones.

The control system 100 may further include a system bus 1006 to facilitate appropriate data communication and processing information between the various components of the computer 1000. The system bus 1006 may be any of several types of bus structures, including a memory bus or memory controller, a peripheral bus, or a local bus using any of a variety of bus architectures. In particular embodiments, the system bus 1006 may facilitate data and information communication between the various components (whether internal or external to the computer 1000) through interfaces.

In still other embodiments, the computer 1000 may further include system memory 1008 with computer storage media such as volatile and non-volatile memory, ROM, and/or RAM. A basic input/output system (BIOS) with appropriate computer-based routines assists in transferring information between components within the computer 1000 and can be stored in ROM. The RAM portion of the system memory 1008 typically contains data and program modules that are immediately accessible to or presently being operated on by processing unit 1004 such as an operating system, application programming interfaces, application programs, program modules, program data, and other instruction-based computer-readable code.

The computer 1000 may also include other removable or non-removable, volatile or non-volatile computer storage media products. For example, the computer 1000 may include a non-removable memory 1010 that communicates with and controls a hard disk drive 1012, i.e., a non-removable, non-volatile magnetic medium. The computer 1000 may further include removable, non-volatile memory interface 1014 that communicates with and controls a magnetic disk drive unit 1016 (which reads from and writes to a removable, non-volatile magnetic disk 1018), an optical disk drive unit 1020 (which reads from and writes to a removable, non-volatile optical disk, such as a CD ROM 1022), a Universal Serial Bus (USB) port for use in connection with, for example, a removable memory card 1023. Other removable or non-removable, volatile or non-volatile computer storage media can be used, including, but not limited to, magnetic tape cassettes, DVDs, digital video tape, solid state RAM, solid state ROM, and the like. These removable or non-removable, volatile or non-volatile magnetic media are in communication with the processing unit 1004 and other components of the computer 1000 via the system bus 1006. The drives and their associated computer storage media provide storage of operating systems, computer-readable instructions, application programs, data structures, program modules, program data, and other instruction-based computer-readable code for the computer 1000 (whether duplicative or not of the information and data in the system memory 1008).

In some embodiments, the computer 1000 may include one or more discrete computer-readable media components or other media that can be accessed by the computer 1000, such as volatile media, non-volatile media, removable media, non-removable media, and the like. In certain embodiments, the computer-readable media be stored in computer he storage medium including, but not limited to, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 1000. In some embodiments, the computer-readable media may include communications media, such as computer-readable instructions, data structures, program modules, or other data in a modulated data signal such as a carrier wave or other transport mechanism. In other embodiments, the computer-readable media may include any information delivery media, wired media (such as a wired network and a direct-wired connection), and wireless media (such as acoustic signals, radio frequency signals, optical signals, infrared signals, biometric signals, bar code signals, etc.). Combinations of any of the above are also included within the scope of computer-readable media.

In particular embodiments, the system 10 may be configured to allow a user to enter commands, information, and data into the computer 1000 using the touch-screen of the GUI display 13 via an operator input interface 1028. In other embodiments, an operator may enter commands, information, and data into the computer 1000 using other attachable or operable input devices, such as a keyboard 1024, a mouse 1026, a remote control device, a microphone, a trackball, a joystick, a touchpad, a scanner, a tablet computer, and the like, via the operator input interface 1028. Any arrangement that facilitates the input of data and information to the computer 1000 from an outside source may be used including, for example, hard wiring or accessing using a wireless network device, such as blue tooth, a wireless internet connection, or a cellular connection. As discussed, these and other input devices are often connected to the processing unit 1004 through the operator input interface 1028 coupled to the system bus 1006, but may be connected by other interface and bus structures, such as a parallel port, game port, or a USB.

The computer 1000 may operate in a network environment 1038 through the use of a communications device 1040, which is integral to the computer or remote. This communications device 1040 is operable by and in communication with the other components of the computer 1000 through a communications interface 1042. Using such an arrangement, the computer 1000 may connect with or otherwise communicate with one or more remote computers, such as a remote computer 1044 of an external information system, which typically includes many or all of the components described above in connection with the computer 1000. Using appropriate communications devices 1040 such as, for example, a modem, a network interface, adapter, telephone line, cellular telephone connection, wifi network, and the like, the computer 1000 may operate within and communicate through a local area network (LAN) and a wide area network (WAN), but may also include other networks such as a virtual private network (VPN), an office network, an enterprise network, an intranet, the Internet, and the like and combinations thereof. It will be appreciated that the network connections shown are exemplary and other means of establishing a communications link between the computers 1000, 1044 may be used.

Generally, the system of embodiments described above may be configured to deliver a radiopharmaceutical drawn from an amount of radiopharmaceutical sufficient for delivery to multiple subjects. In some embodiments, the user may input the radioactive emissions of the radiopharmaceutical contained in the volume of radiopharmaceutical in to the control system when the radiopharmaceutical is loaded into the system 10. The system may be configured to determine the volume of radiopharmaceutical and to deliver a dose of radiopharmaceutical having a desired activity level based on the measured amount of radioactive activity. The system may then administer the proper amount of radiopharmaceutical to deliver the appropriate dose of radiopharmaceutical as identified by the user to the subject. The system may further monitor the decay of the radiopharmaceutical or optical tracer over time, either by intermittent measurements carried out by an on-board sensor, such as a Geiger counter or optical sensor, or based on the calculated decay based on the rate of decay for the particular isotope used in the radiopharmaceutical or the fluorophore used in a particular optical tracer.

The fluid delivery system 10 may further be configured for priming (i.e., purging air from the tubing system) and delivering a radiopharmaceutical to a subject, while minimizing or eliminating exposing the individuals operating the system to the radiopharmaceutical and minimizing or eliminating contaminated waste. Moreover, the delivery system 10 may facilitate safe delivery of the pharmaceutical to multiple destinations (for example, dose delivery to a series of subjects).

The system 10 may be further configured to provide feedback information to the operator. For example, in some embodiments, the system may provide the operator with information regarding the administration such as, but not limited to, the dosage of radiopharmaceutical delivered to the subject by milligram (mg), volume (ml), and/or radioactive activity (mCi), dosing time (i.e., the time required for delivery), the delivery time (i.e., the time of day), date, and the fluid pressure in the delivery system during delivery. In some embodiments, the system may reference subject data to determine the amount of radiopharmaceutical administered to the particular subject over time and provide a warning to the operator if absorbed levels become too high. In various embodiments, the information may be provided to the operator in real time.

Following administration or the completion of an administration protocol, the system may provide a summary of the procedure including any relevant data. For example, in various embodiments, the system may provide the dosage of radiopharmaceutical delivered to the subject by milligram (mg), volume (ml), and/or radioactive activity (mCi), the amount of other pharmaceutical composition delivered to the subject (mg/ml), dosing time (i.e., the time required for delivery), the delivery time (i.e., the time of day), date, and the fluid pressure in the delivery system during delivery, and the like and combinations thereof. The data provided either in real time during performance of the protocol or in summary of the procedure may be provided numerically or graphically, and in certain embodiments, the screens providing the data may provide both numeric and graphic data simultaneously.

The system may further provide subject identification and any critical data such as, weight, age, disease being treated or tested for, the procedure to be performed, the location of the injection/infusion site, and the like and various combinations thereof. Such data may be inputted at the time of the procedure or may be inputted prior to the procedure. In certain embodiments, the operator may input subject identification and the system may retrieve appropriate subject data from electronically archived records using a computer network or Internet connection. In still further embodiments, the system may store subject information for more than one procedure.

The systems of various embodiments may be configured to deliver any radiopharmaceutical known in the art, and the radiopharmaceutical may be delivered alone or in combination with another pharmaceutical composition. For example, in some embodiments, the system may be designed and configured to deliver $^{47}Ca$—$Ca^{2+}$, $^{11}C$-L-methyl-methionine, $^{14}C$-glycocholic acid, $^{14}C$-para-amino benzoic acid (PABA), $^{14}C$-urea, $^{14}C$-d-xylose, $^{51}Cr$-red blood cells, $^{51}Cr$—$Cr^{3+}$, $^{51}Cr$-ethylenediaminetetraacetic acid (EDTA), $^{57}Co$-cyanocobalamin (vitamin $B_{12}$), $^{58}Co$-cyanocobalamin (vitamin $B_{12}$), $^{169}Er$-colloid, $^{18}F$-fluorodeoxyglucose (FDG), $^{18}F$-fluoride, $^{18}F$-fluorocholine, $^{68}Ga$-dotatoc or dotatate, $^{3}H$-water, $^{111}In$-diethylenetriaminepenta-acetic acid (DTPA), $^{111}In$-leukocytes, $^{111}In$-platelets, $^{111}In$-pentetreotide, $^{111}In$-octreotide, $^{123}I$-iodide, $^{123}I$-o-iodohippurate, $^{123}I$-m-iodobenzylguanidine (MIBG), $^{123}I$-FP-CIT, $^{125}I$-fibrinogen, $^{131}I$-iodide, $^{131}$-iodide, $^{131}I$-m-iodobenzylguanidine (MIBG), $^{59}Fe$—$Fe^{2+}$ or $Fe^{3+}$, $^{81m}Kr$-aqueous, $^{13}N$-ammonia, $^{15}O$-water, $^{32}P$-phosphate, $^{82}Rb$-chloride, $^{153}Sm$-ethylenediaminotetramethylenephosphoric acid (EDTMP), $^{75}Se$-selenorcholesterol, $^{75}Se$-23-Seleno-25-homo-tauro-cholate (Se-HCAT), $^{22}Na$—$Na^{+}$, $^{24}Na$—$Na^{+}$, $^{89}Sr$-chloride, $^{99m}Tc$-pertechnetate, $^{99m}Tc$-human albumin, $^{99m}Tc$-human albumin macroaggregates or microspheres, $^{99m}Tc$-phosphonates and phosphate, $^{99m}Tc$-diethylenetriaminepenta-acetic acid (DTPA), $^{99m}Tc$-dimercaptosuccinic acid (V) (DMSA), $^{99m}Tc$-dimercaptosuccinic acid (III) (DMSA), $^{99m}Tc$-colloid, $^{99m}Tc$-hepatic iminodiacetic acid (HIDA), $^{99m}Tc$-denatured red blood cells, $^{99m}Tc$-red blood cells, $^{99m}Tc$-mercaptoacetyltriglycine (MAG3), $^{99m}Tc$-exametazime, $^{99m}Tc$-sestamibi (MIBI-methoxy isobutyl isonitrile), $^{99m}Tc$-sulesomab (IMMU-MN3 murine Fab'-SH antigranulocyte monoclonal antibody fragments), $^{99m}Tc$-human immunoglobulin, $^{99m}Tc$-tetrofosmin, $^{99m}Tc$-ethyl cysteinate dimer (ECD), $^{201}Tl$—$Tl^{+}$, $^{133}Xe$ in isotonic sodium chloride solution, $^{90}Y$-silicate, and the like and combinations thereof. In certain embodiments, the system may be configured for delivery of radiopharmaceuticals for imaging myocardial or other cardiovascular conditions. In such embodiments, the system may be configured to deliver $^{18}$F-fluorodeoxyglucose (FDG), $^{13}$N-ammonia, $^{15}$O-Water, $^{82}$Rb-Chloride, $^{99m}$Tc-pertechnetate, $^{99m}$Tc-human albumin, $^{99m}$Tc-human albumin macroaggregates or microspheres, $^{99m}$Tc-diethylenetriaminepenta-acetic acid (DTPA), $^{99m}$Tc-denatured red blood cells, $^{99m}$Tc-red blood cells, $^{99m}$Tc-exametazime, $^{99m}$Tc-sestamibi (MIBI—methoxy isobutyl isonitrile), $^{19m}$Tc-tetrofosmin, $^{201}$Tl—Tl$^+$, and the like and combinations thereof.

Optical tracers used in various embodiments, may be derived from any source. For example, in some embodiments, the optical tracer may be a fluorochrome, green fluorescent protein, red fluorescent protein, and luciferin or any other bioluminescent molecule isolated from, for example, ctenophores, coelenterases, mollusca, fish, ostracods, insects, bacteria, crustacea, annelids, and earthworms. In particular embodiments, the optical tracer may be isolated from fireflies, Mnemiopsis, Beroe ovata, Aequorea, Obelia, Pelagia, Renilla, Pholas Aristostomias, Pachystomias, Poricthys, Cypridina, Aristostomias, Pachystomias, Malacosteus, Gonadostomias, Gaussia, Watensia, Halisturia, Vampire squid, Glyphus, Mycotophids, Vinciguerria, Howella, Florenciella, Chaudiodus, Melanocostus, Sea Pens, Chiroteuthis, Eucleoteuthis, Onychoteuthis, Watasenia, cuttlefish, Sepiolina, Oplophorus, Acanthophyra, Sergestes, Gnathophausia, Argyropelecus, Yarella, Diaphus, Gonadostomias, Ptilosarcus, or Neoscopelus, and in certain embodiments, the optical tracer may be luciferin or coelentrazine.

In some embodiments, the system may be configured to administer a single radiopharmaceutical composition, and in other embodiments the system may be configured to deliver two or more different radiopharmaceuticals. In embodiments in which the system is configured to deliver multiple radiopharmaceuticals, the system may allow the operator to switch configurations depending on the intended procedure. The amount of radiopharmaceutical delivered by the system may vary among embodiments and based on the protocol being used. Generally, a technician or other qualified personnel can determine an appropriate amount of the radiopharmaceutical to be delivered to a particular subject using metrics regarding the subject known in the art. Because of the flexibility of the system, any amount of radiopharmaceutical can be delivered.

User control of the system 10 can be carried out by any suitable means. For example, in some embodiments, a user may trigger delivery of the radiopharmaceutical using the GUI interface by pressing a button on the screen. In other embodiments, an external button may be used to trigger delivery. The external button may be configured to be activated, for example, by hand or using a foot pedal. In some embodiments, the system may include an interrupt button that is configured to allow an operator to pause or abort an injection procedure in the event of, for example, subject discomfort or an emergency, while by-passing the GUI display 13, which also can be configured to allow the user to pause or abort an injection procedure. An interrupt button may be connected to LEDs and/or a printed circuit board to provide visual and/or auditory alarms when the interrupt button has been activated.

Various embodiments are directed to methods for using the system and devices encompassed by the system. In some embodiments, before starting the injection procedure, the operator may determine, i) the desired amount of radiopharmaceutical to be delivered to the subject based on the activity of the radiopharmaceutical and ii) the estimated concentration of activity in the vial (i.e., the activity per unit of volume, MBq/ml). These data may be provided to the system controller. In other embodiments, data provided to the controller may further include, the type of radiopharmaceutical provided in the system, subject identification. The methods of various embodiments may include the step of inputting such information before beginning the procedure.

In certain embodiments, methods may further include generating a list of procedures to be performed over a time period. While the information provided in such a list may vary, in some embodiments, the list may include subject ID numbers, type of procedure, amount of radiopharmaceutical to be delivered to the identified subject, the time necessary of the procedure and/or a projected start time for the procedure, and the like. In particular embodiments, the information required for such a list may be inputted into the system before initiation, and in other embodiments, information for the list may be provided before the initiation of the procedure for each individual subject. In still other embodiments, information for the list may be inputted remotely, and subject information may be provided to the system via an Internet or other network connection.

Initialization may include any number of steps necessary to prepare the system for delivery of a radiopharmaceutical. In some embodiments, initialization may include the step of filling the system including all tubing and connectors with saline or another medical fluid to remove air from the fluid path i.e., flushing the system. In some embodiments, the step of flushing the system may be carried out by manually filling the tube set 50 with saline before connecting to a syringe including radiopharmaceutical. In other embodiments, the tube set 50 and various portions thereof may be prefilled with saline or another medical fluid before packaging.

After flushing, such methods may include the step of introducing a radiopharmaceutical into the system. The volume of the radiopharmaceutical in the syringe may be inputted into the control system, or in other embodiments, the system may use an internal protocol to determine the volume of the radiopharmaceutical in the syringe using, for example, the switch method described above. In still other embodiments, the user may input the average radioactive emissions from the radiopharmaceutical sample introduced into the system. In some embodiments, the user may determine the volume of radiopharmaceutical to be delivered, and the motor or pump may deliver an appropriate volume of radiopharmaceutical when prompted by the user. In other embodiments, the amount of radiopharmaceutical to be delivered to a subject based on the radioactive emissions from the radiopharmaceutical, and the control system may determine an appropriate volume of radiopharmaceutical to be delivered based on the emissions provided by the user or determined internally using, for example, an internal Geiger counter, and the volume of radiopharmaceutical in the syringe. The motor or pump may deliver an appropriate amount of radiopharmaceutical when prompted by the user.

In various embodiments, the method presented above may further include the step of delivering the radiopharmaceutical to the subject. Delivering the radiopharmaceutical may include the steps of inserting a needle or other delivery device into the subject at an appropriate location such a vein or artery. For mice, the tail vein is commonly used. The user may then secure the needle to the subject using, for example, medical tape, and the needle and needle tube may be primed to introduce blood into the needle and needle tube. A primed extension tube or primed diffusion chamber may then be connected to the needle and needle tube to provide a wet-wet connection. The radiopharmaceutical can then be delivered to the subject by activating the motor or pump causing the plunger to be advanced delivering the appropriate volume of radiopharmaceutical to the subject.

In some embodiments, another injection of the radiopharmaceutical may then be delivered to the same or a different subject. In such embodiments, procedure may continue by repeating the steps provided above. Notably, the initialization steps may be omitted during repeated delivery of radiopharmaceutical. In some embodiments, the system may determine the relative emission of radioactivity of the radiopharmaceutical over time based on decay of the radioactive component of the radiopharmaceutical and adjust the volume of radiopharmaceutical administered to make-up for decay. Thus, each subject may be provided with the identical amount of radiopharmaceutical based on radioactive emission. In the event that no further injections are necessary, the procedure may be terminated using a shutdown protocol, which may include one or more steps of flushing the system with medical fluid.

Figure 11:

The display 13 of some embodiments may be a graphical user interface (GUI) allowing for easy and logical entry of information for injection operation. For example, in particular embodiments, the user may be prompted for information related to the fluid supply that will be loaded on to the injector via a screen similar to that shown in FIG. 11. When the "Syringe" button located at the upper left is pressed, the screen presented in FIG. 12 may appear, which allows the user to enter specific information related to the drug that can be loaded on to the injector in a syringe. This information may include, for example, but is not limited to, syringe size, drug name, fluid type, lot number, date, and time and radioactivity level at assay time (if the drug is a radiopharmaceutical).

Figure 13:
Figure 14:
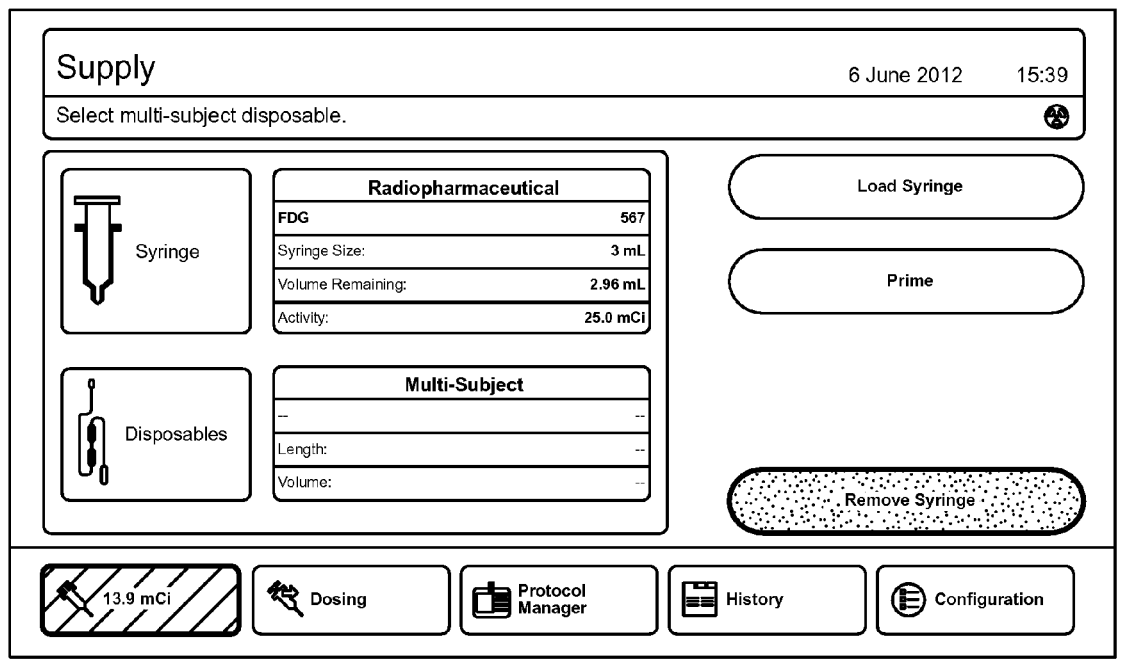
Figure 15:
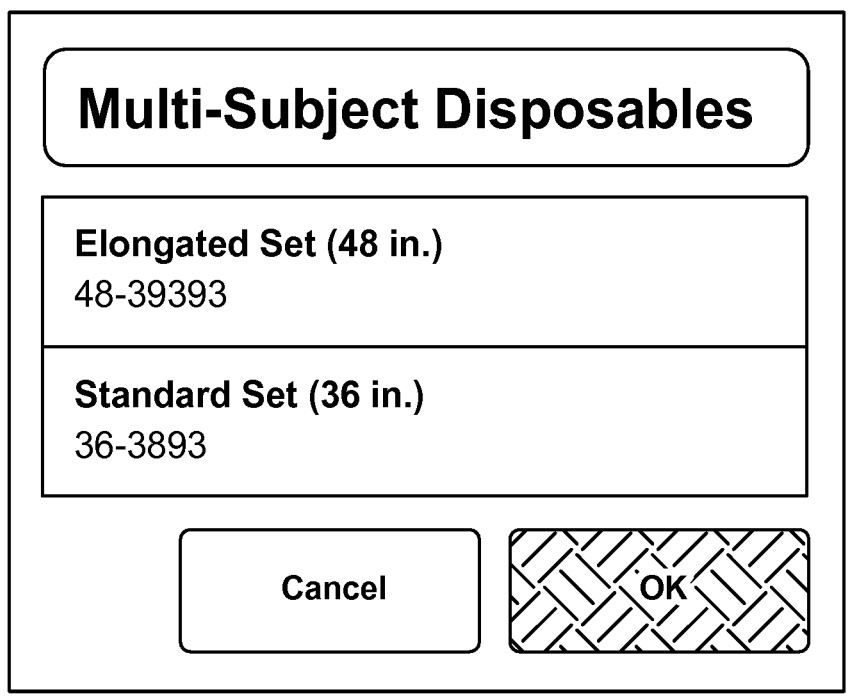
Figure 16:
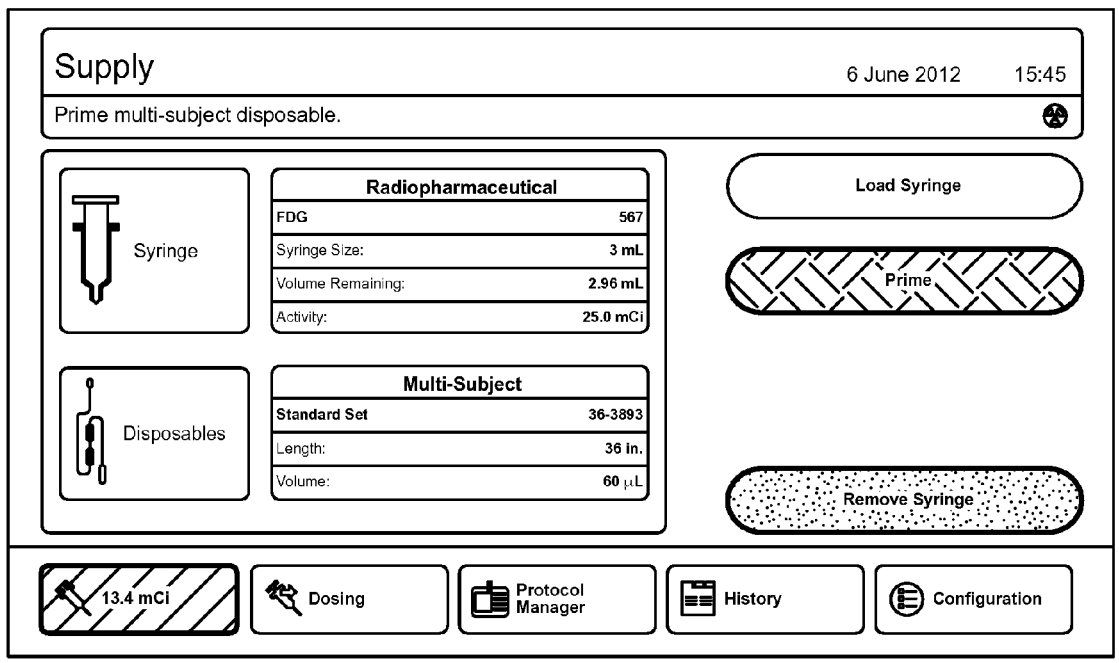
Figure 17:
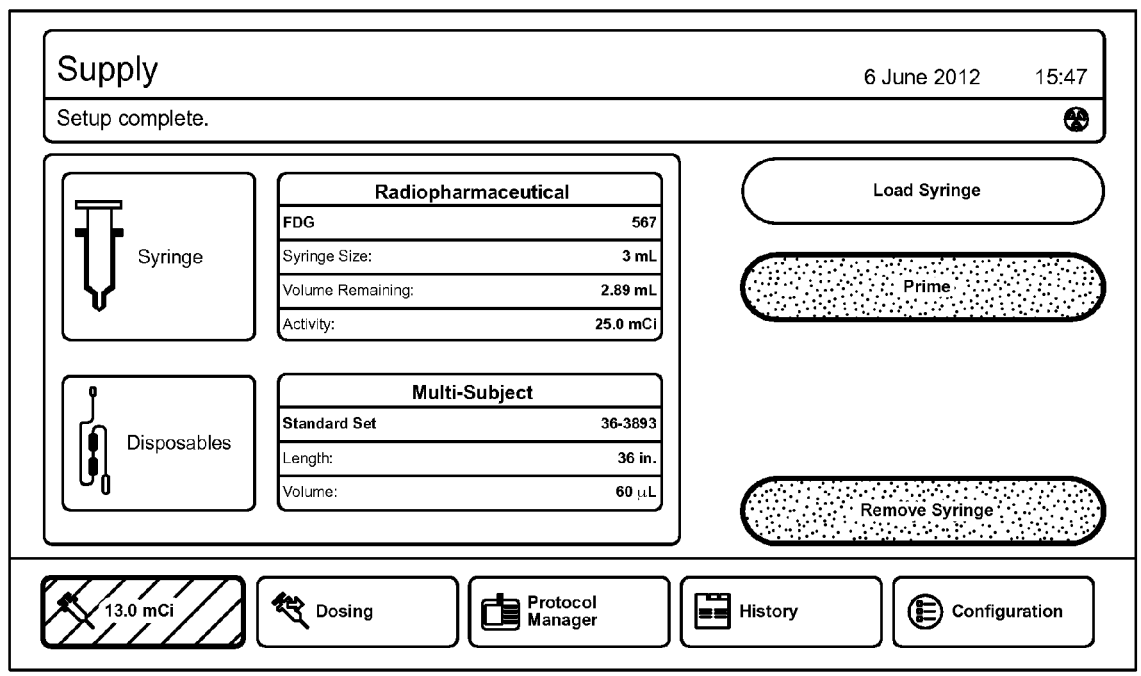

After saving this information, the user is then prompted to load the syringe on the injector as shown in FIG. 13. After pressing the "Load Syringe" button, the piston in the injector advances forward to contact the plunger of the syringe. At this point, the user may be prompted to select a multi-subject disposable tubing set as shown in FIG. 14. Upon pressing the "Disposables" button located at the lower left, the screen shown in FIG. 15 may appear. The user selects one of the choices and presses "OK." As shown in FIG. 16, the system may prompt the user to prime the selected multi-subject disposable tubing set. After pressing the "Prime" button, the injector's piston is advanced forward to move fluid into the multi-subject disposable set to displace air that is present in the system. After priming is completed, the screen shown in FIG. 17 may appear indicating that the system setup is now complete.

Figure 18:
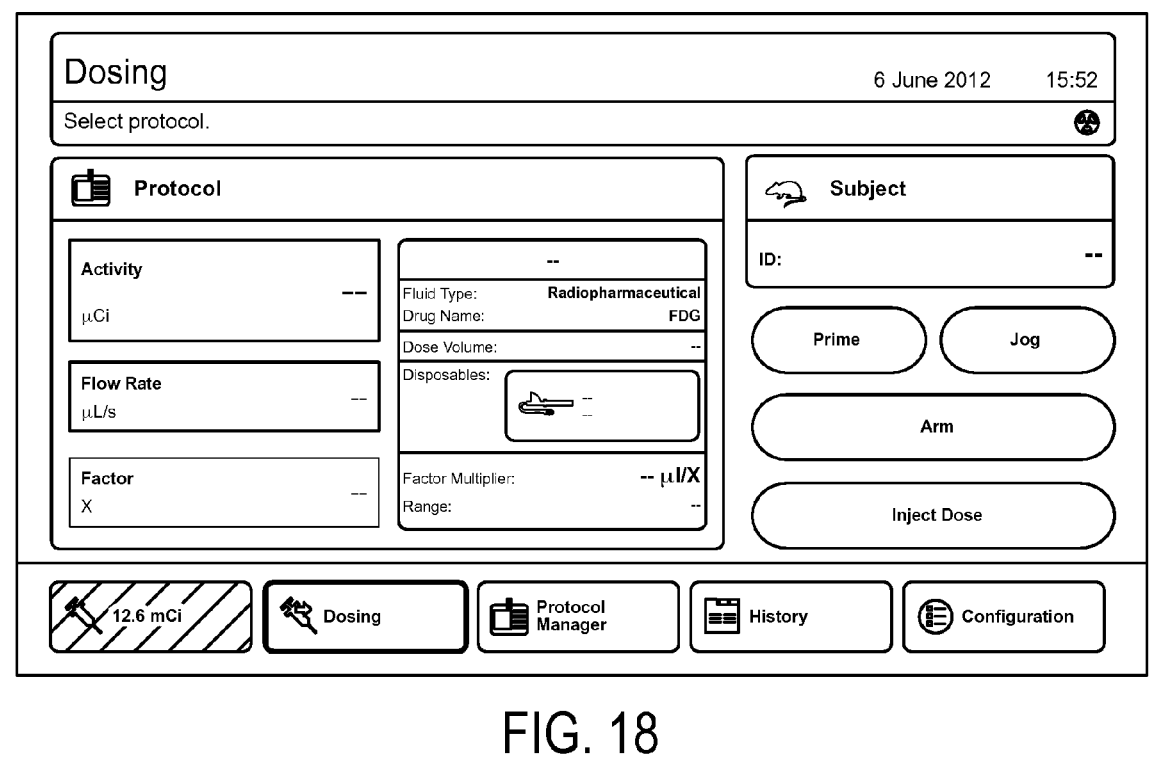
Figure 19:
Figure 20:
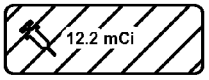
Figure 22:
Figure 23:

Following setup, the user may be provided a screen that includes a Dosing button that when pressed causes the screen shown in FIG. 18 to appear. This screen prompts the user to select a protocol (i.e., a set of injection parameters) by pressing the "Protocol" button located at the mid-left of the screen. This action may result in the screen shown in FIG. 19 appearing to, allow the user to select a stored protocol to be executed. After selecting a protocol, the screen shown in FIG. 20 may appear, which then prompts the user to enter information on the subject to be injected. When the user presses the "Subject" button located at the upper right, the screen shown in FIG. 21 may appear. This screen allows the user to enter specific information related to the subject to be injected. This information may include, for example, but is not limited to, subject ID, alternate ID, gender, and animal type. After saving this information, the user is then prompted to prime the per-subject disposable by the "prime" button being highlighted or color shaded. After pressing the "Prime" button, the injector's piston is advanced forward to move fluid into the per-subject disposable set to displace air that is present in the system. After priming is completed, the screen shown in FIG. 22 is shown that indicates that the system is now ready to inject. At this point, the "Arm" button is highlighted, or color-shaded, to indicate to the user that this button must be pressed next to energize the system to allow an injection. After the "Arm" button is pressed, the screen shown in FIG. 23 is displayed. The "Inject Dose" button is highlighted, or color-shaded, to indicate to the user that this button must be pressed next to actually start the injection. After this button is pressed, the injection takes place. When the injection completes, the screen shown in FIG. 24 may appear. This screen shows the dose and volume that was actually delivered by the injector. This screen may also show other information related to the injection that may be important to the user. This screen may allow this information to be transferred to a printer attached to the system for archival purposes.

Figure 25:
Figure 26:
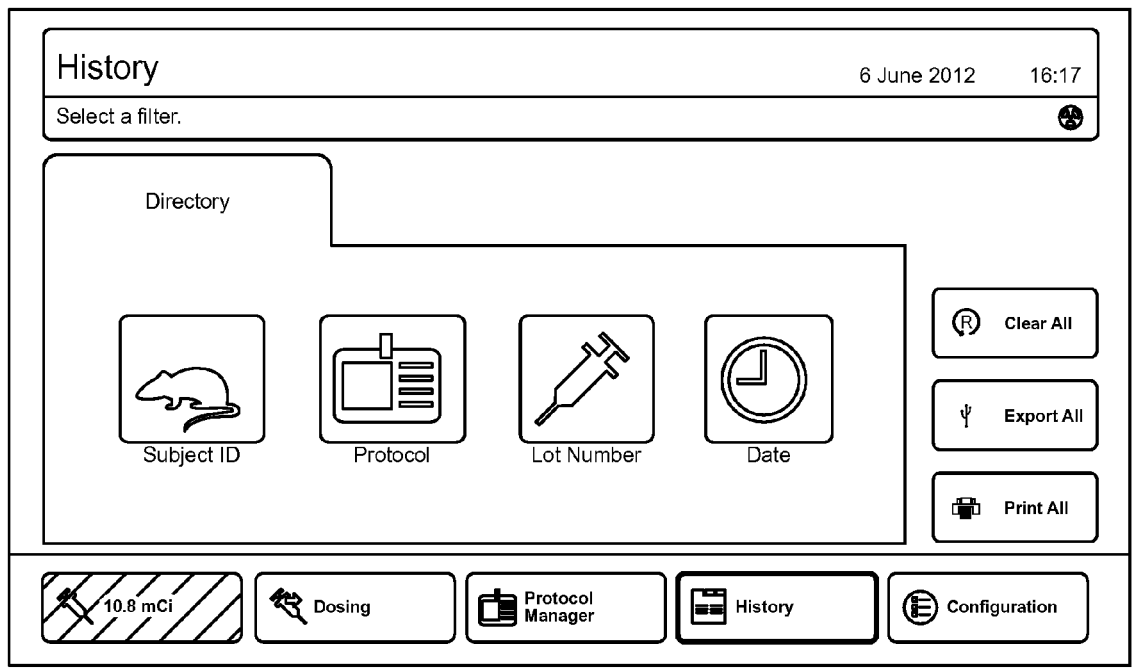

Other screens within the GUI may allow other functions to be performed by the user. For example, FIG. 25 shows a screen that allows protocols to be entered and edited as part of a protocol management function. As another example, FIG. 26 shows a screen that allows the stored information from completed injections to be sorted by subject ID, protocol, lot number or date, for instance.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

The invention claimed is:

1. A needle handle comprising:
    a needle handle body configured to connect to a portion of a needle; and
    a pair of separated wings attached to and extending from the needle handle body, wherein the wings are sized and shaped to be grasped by a user,
    wherein the needle handle body further comprises a breakable cleft opposite an attachment of the pair of separated wings to the needle handle body, and
    wherein the needle handle body is configured to be broken along the cleft and separated from the needle after insertion of the needle into a subject.

2. The needle handle of claim 1, further comprising a needle tubing section, the needle tubing section comprising a connector opposite the needle handle.

3. The needle handle of claim 1, wherein the needle handle body includes a c-shaped bore sized to accommodate a needle tubing section, wherein a portion of the needle tubing section is exposed through the needle handle.

4. The needle handle of claim 3, wherein the c-shaped bore is opposite the pair of separated wings.

5. The needle handle of claim 3, wherein the c-shaped bore is offset from the pair of separated wings.

6. The needle handle of claim 1, wherein the pair of separated wings are configured to be removed after insertion of the needle into a subject.

7. The needle handle of claim 1, wherein the pair of separated wings are attached to the needle with a breakable connector.

8. The needle handle of claim 1, wherein the pair of separated wings are configured to provide a surface area for stable attachment of the needle handle to a subject using a medical tape.

9. A needle handle comprising:
a needle handle body configured to connect to a portion of a needle, the needle handle body having a proximal end which connects to the portion of the needle and a distal end through which a needle tubing section extends, the needle handle body further comprising a c-shaped bore sized to accommodate the needle tubing section extending between the distal end and the proximal end; and
a single wing or fin attached to and extending from the needle handle body and disposed between the proximal end and the distal end, wherein the single wing or fin is sized and shaped to be grasped by a user.

10. The needle handle of claim 9, wherein a portion of the needle tubing section is exposed through the needle handle.

11. The needle handle of claim 9, wherein the c-shaped bore is opposite the wing or fin.

12. The needle handle of claim 9, wherein the c-shaped bore is offset from the wing or fin.

13. The needle handle of claim 9, wherein the wing or fin is configured to be removed after insertion of the needle into a subject.

14. The needle handle of claim 9, wherein the wing or fin is attached to the needle with a breakable connector.

15. The needle handle of claim 9, wherein the wing or fin is configured to provide a surface area for stable attachment of the needle handle to a subject using a medical tape.

16. The needle handle of claim 9, further comprising a ventral enclosure positioned at the distal end of the needle handle, wherein the ventral enclosure forms an opening through which the needle tubing section extends.

* * * * *